US012766207B2

(12) United States Patent
Wang et al.

(10) Patent No.: US 12,766,207 B2
(45) Date of Patent: Oct. 20, 2026

(54) STERILIZATION AND DEODORIZATION WASTE CONTAINER

(71) Applicant: Shi Ping Wang, Ontario, CA (US)

(72) Inventors: Shi Ping Wang, Ontario, CA (US); Jiangqun Chen, Fuzhou (CN); Youxi Lou, Fuzhou (CN); Zhou Lin, Fuzhou (CN)

(73) Assignees: Fujian Nashida Electronic Incorporated Company, Fuzhou (CN); Nine Stars Group (U.S.A.) Inc., Ontario (CA)

( * ) Notice: Subject to any disclaimer, the term of this patent is extended or adjusted under 35 U.S.C. 154(b) by 311 days.

(21) Appl. No.: 18/634,951

(22) Filed: Apr. 14, 2024

(65) Prior Publication Data

US 2024/0390534 A1 Nov. 28, 2024

Related U.S. Application Data

(63) Continuation-in-part of application No. 18/222,383, filed on Jul. 14, 2023, and a continuation-in-part of (Continued)

(51) Int. Cl.
*A61L 2/10* (2026.01)
*A61L 2/202* (2026.01)
(Continued)

(52) U.S. Cl.
CPC ................. *A61L 2/10* (2013.01); *A61L 2/202* (2013.01); *A61L 2/24* (2013.01); *A61L 2/26* (2013.01); *A61L 9/015* (2013.01); *A61L 9/20* (2013.01); *B65F 1/02* (2013.01); *B65F 1/163* (2013.01); *B65F 1/1638* (2013.01); *B65F 1/1646* (2013.01); *A61L 2101/02* (2020.08); *A61L 2103/23* (2026.01); *A61L 2202/11* (2013.01);
(Continued)

(58) Field of Classification Search
CPC ... A61L 2/10; A61L 2/202; A61L 2/24; A61L 9/20; B65F 1/1638
See application file for complete search history.

(56) References Cited

U.S. PATENT DOCUMENTS 5,337,581 A * 8/1994 Lott ........................ A61L 11/00 422/292
2007/0295355 A1* 12/2007 Ikuta .................. H10P 72/0406 134/1

FOREIGN PATENT DOCUMENTS

CN 204727000 U * 10/2015
CN 110733785 A * 1/2020 ................ B65F 1/14

* cited by examiner

*Primary Examiner* — Jennifer Wecker
*Assistant Examiner* — Brady C Pilsbury
(74) *Attorney, Agent, or Firm* — David & Raymond Patent Firm; Raymond Y Chan

(57) ABSTRACT

A sterilization and deodorization waste container includes an isolation chamber provided on an inner side of a container lid and a dual-band ultraviolet lamp tube installed in the isolation chamber. The dual-band ultraviolet lamp tube is capable of simultaneously generating a direct ultraviolet light wave and an ozone ultraviolet light wave. The isolation chamber includes a reflector housing having a light transmitting window facing an inner cavity of a container body. The dual-band ultraviolet lamp tube is controlled by a control circuit to turn on to generate the ultraviolet light rays into an inner cavity of the container body while the container lid is closed and to turn off to stop generating the ultraviolet while the container lid is opened.

12 Claims, 14 Drawing Sheets

Related U.S. Application Data application No. 18/266,587, filed on Jun. 9, 2023, now Pat. No. 12,617,609, and a continuation-in-part of application No. 18/204,945, filed on Jun. 2, 2023, now abandoned, and a continuation-in-part of application No. 17/357,770, filed on Jun. 24, 2021, now Pat. No. 12,084,277.

(51) Int. Cl.

| | |
|---|---|
| ***A61L 2/24*** | (2006.01) |
| ***A61L 2/26*** | (2006.01) |
| ***A61L 9/015*** | (2006.01) |
| ***A61L 9/20*** | (2006.01) |
| ***A61L 101/02*** | (2006.01) |
| ***A61L 103/00*** | (2026.01) |
| ***B65F 1/02*** | (2006.01) |
| ***B65F 1/16*** | (2006.01) |

(52) U.S. Cl.

CPC ... *A61L 2202/121* (2013.01); *A61L 2202/122* (2013.01); *A61L 2202/14* (2013.01); *A61L 2209/111* (2013.01); *A61L 2209/12* (2013.01); *A61L 2209/212* (2013.01); *B65F 2210/129* (2013.01); *B65F 2210/168* (2013.01)

STERILIZATION AND DEODORIZATION WASTE CONTAINER

CROSS REFERENCE OF RELATED APPLICATION

This application is a Continuation-In-Part application that claims the benefit of priority under 35 U.S.C. § 120 to a non-provisional application, application Ser. No. 17/357,770, filed Jun. 24, 2021, a non-provisional application, application Ser. No. 18/266,587, filed Jun. 9, 2023, a non-provisional application, application Ser. No. 18/204,945, filed Jun. 2, 2023, and a non-provisional application, application Ser. No. 18/222,383, filed Jul. 14, 2023, which is a Continuation-In-Part application that claims the benefit of priority under 35 U.S.C. § 120 to a non-provisional application, application Ser. No. 18/266,587, filed Jun. 9, 2023, which are incorporated herewith by references in their entireties.

BACKGROUND OF THE PRESENT INVENTION

Field of Invention

The present invention relates to a sterilization and deodorization waste container, in particular a sterilization and deodorization waste container with dual-band ultraviolet lamp tube. Further, the present invention also relates a control method of induction waste container with cold cathode ultraviolet lamp sterilization and deodorization, which is adapted for the control of infrared induction circuit that is capable of sterilizing and deodorizing simultaneously by means of ultraviolet sterilization and ozone sterilization with dual-band ultraviolet lamp tube.

Description of Related Arts

Current household waste containers are generally equipped with lids configured to be opened by means of foot pedal, induction, gentle touch and etc. In particular, in the waste container used in the kitchen, the kitchen waste disposed in the container is easy to breed bacteria and generate stinky smell, resulting in pollution of people's living environment, affecting the olfactory sensation and health of the users, and causing potential sanitation hazards. That further affects people's sense of smell and health and has health hazards.

In order to solve the above problems, the current technology utilizes ultraviolet light wave for sterilization. That is, a direct ultraviolet lamp tube is installed in the waste container to sterilize the interior environment in the container, but this solution of using ultraviolet for direct sterilization has the following shortcomings:

1. The ultraviolet directly irradiated by ultraviolet lamp tube for direct sterilization can only propagate linearly along a straight line and cannot reach many positions when used for sterilization in the waste container, and thus there are more positions that cannot be irradiated and dead angles during the sterilization in the container. Therefore, its sterilization effect is relatively poor.
2. In order to ensure light transmission and sterilization effect, the ultraviolet lamp tube in the current technology often adopts a naked installation method. That is, the ultraviolet lamp tube is arranged to face the interior of the container without obstruction. Due to the harsh environment within the container, the operating condition of the ultraviolet lamp tube is adversely affected directly, so that its service life span is also greatly shortened, the cost of use is high, and it is difficult to promote.

In addition, most of the conventional sterilization and deodorization waste containers adopt either the ozone method or the ultraviolet irradiation method. However, only a single method is used to sterilize and deodorize the effect is not effective enough. Also, most of the conventional ultraviolet lamps are in the working state without stopping when the lid is closed and standby. On the one hand, it can greatly affect the service life of the cold cathode ultraviolet lamp and increase the cost of utilization. Also, the excessive ozone generated by long-term work will diffuse and affect the environment, resulting in safety and health problems.

SUMMARY OF THE PRESENT INVENTION

In view of the shortcomings of the current technology, an objective of the invention is to provide a sterilization and deodorization waste container equipped with a dual-band ultraviolet lamp tube, that avoids sterilization dead angle, enhances the sterilization effect, improves the operating environment of the ultraviolet lamp, improves service life span thereof, and reduces the cost of use.

Another objective of the invention is to provide a sterilization and deodorization waste container which automatically processes sterilization and deodorization while the container lid thereof is in close state and stops sterilization and deodorization while the container lid thereof is in open state or the container lid is detached from the container body.

Another objective of the invention is to provide a sterilization and deodorization waste container equipped with a dual-band ultraviolet sterilization and deodorization arrangement which is adapted to be arranged at or above a container opening of the inner cavity of the waste container and configured for propagating ultraviolet light rays in the inner cavity of the container body for sterilization and deodorization of the waste contained in the inner cavity of the container body.

Another objective of the invention is to provide a sterilization and deodorization waste container equipped with a dual-band ultraviolet sterilization and deodorization arrangement which is adapted to be installed in the container lid and configured for propagating ultraviolet light rays in the inner cavity of the container body for sterilization and deodorization of the waste contained in the inner cavity.

Another objective of the invention is to provide a dual-band ultraviolet sterilization and deodorization arrangement which is appliable to all types of waste container, including foot pedal waste container, induction waste container, touch waste container, and etc.

Another objective of the invention is to provide a dual-band ultraviolet sterilization and deodorization arrangement for waste container, which is automatically operated to start generating ultraviolet light rays and stop generating ultraviolet light rays according to the closing and opening of the container lid and/or the cover panel with respect to the container body.

Another objective of the invention is to provide a dual-band ultraviolet sterilization and deodorization arrangement for waste container having an inner cavity for storing waste, which comprises an ultraviolet generator and a control means, wherein the ultraviolet generator comprises a dual-band ultraviolet lamp tube arranged in the waste container and configured to generate ultraviolet light rays with a high frequency direct sterilization ultraviolet light wave propagating directly to the inner cavity of the waste container for direct sterilization and an ozone sterilization ultraviolet light wave dispersing and diffusing in the inner cavity of the waste container for ozone sterilization, wherein the control means is arranged for turning off dual-band ultraviolet lamp tube while the inner cavity of the waste container is accessible to outside and turning on the dual-band ultraviolet map tube while the inner cavity waste container is in closed from outside.

Another objective of the present invention is to provide a control method of induction waste container with cold cathode ultraviolet lamp deodorization configured for avoiding signal interference, ensuring the reliability of inductive opening of the container lid and/or cover panel, prolonging the service life of ultraviolet lamp, and ensuring environmental safety in accordance with the shortcomings of the prior art.

Additional advantages and features of the invention will become apparent from the description which follows and may be realized by means of the instrumentalities and combinations particular point out in the appended claims.

According to the invention, the foregoing objectives is attained by:

a sterilization and deodorization waste container, including:

a container body;

a container lid, arranged on the container body, including:

an isolation chamber installed on an inner side of the container lid, wherein the isolation chamber comprises a reflector housing and a transparent window, preferably a transparent quartz glass, an opening of the reflector housing facing an inner cavity of the container body, shape and size of the transparent quartz glass fitting and matching to an opening surface of the reflector housing and being covered and connected to the opening of the reflector housing; and a dual-band ultraviolet lamp tube arranged in the isolation chamber, the dual-band ultraviolet lamp tube being a lamp tube capable of simultaneously generating a direct sterilization ultraviolet light wave and an ozone sterilization ultraviolet light wave; and a control means is adapted for controlling of the dual-band ultraviolet lamp tube to generate the direct sterilization ultraviolet light wave and the ozone sterilization ultraviolet light wave.

In one embodiment, the control means includes a control circuit and a driving circuit of the dual-band ultraviolet lamp tube having a control input terminal connected to a driving control terminal of the control circuit by a control switch.

In one embodiment, the transparent quartz glass is sealingly covered and connected to the opening of the reflector housing though a sealing silicone ring cover.

In accordance with another aspect of the invention, the present invention comprises a dual-band ultraviolet sterilization and deodorization arrangement for a waste container including a container body having a container opening and an inner cavity for storing waste and a container lid configured to be mounted on top of the container opening to cover the inner cavity of the container body, wherein the dual-band ultraviolet sterilization and deodorization arrangement comprises:

an isolation chamber comprising a reflector housing, configured for installing below the container lid of the waste container, having a light-transmitting window formed in a lower side thereof;

a dual-band ultraviolet lamp tube arranged in the reflector housing and configured to generate high frequency ultraviolet light rays, including a direct sterilization ultraviolet light wave having a wave length between 253.7 nm to 254 nm and an ozone sterilization ultraviolet light wave having a wave length between 165 nm to 200 nm, such that the ultraviolet light rays are arranged to propagate out into the inner cavity of the container body through the light-transmitting window; and a control circuit configured to selectively turn on the dual-band ultraviolet lamp tube to propagate the ultraviolet light rays and turn off the dual-band ultraviolet lamp tube to stop propagating the ultraviolet light rays.

In one embodiment, the reflector housing has an opening in the lower side and the light-transmitting window is a transparent quartz glass fittingly and sealingly mounted at the opening of the reflector housing for facing the inner cavity of the container body.

In one embodiment, a reflective surface is provided at an upper side of the reflector housing, wherein a lower side of the dual-band ultraviolet lamp tube sealingly arranged in the isolation chamber faces the light-transmitting window of the isolation chamber and an upper side of the dual side of the dual-band ultraviolet lamp tube faces the reflective surface of the isolation chamber such that a portion of the ultraviolet light rays propagating upward is reflected by the reflecting surface to propagate downwards through the light-transmitting window into the inner cavity of the container body.

In one embodiment, the control circuit is configured to selectively control the dual-band ultraviolet lamp tube to turn off to stop generating the ultraviolet light rays while the container lid is opened with respect to the container body and to turn on to generate the ultraviolet light rays while the container lid is closed with respect to the container body.

In one embodiment, the control circuit comprises at least one detecting control element and at least one control driving element which are installed on the container body and the container lid respectively in such a manner that when the container lid is opened, the control driving element leaves a detection range of the detecting control element, the control circuit controls the dual-band ultraviolet lamp tube to turn off to stop generating the ultraviolet light rays, and that when the container lid is closed in place, the detecting control element detects an approaching of the control driving element and the control circuit controls the dual-band ultraviolet lamp tube to turn on to generate the ultraviolet light rays.

In one embodiment, the detecting control element is selected from a group consisting of Hall element, position limiting switch and an angle sensor.

In one embodiment, the detecting control element is a Hall element and the control driving element is a magnet.

In one embodiment, the control driving element is provided under the container lid and the detecting control element is provided in the waste container where the detecting control element is able to detect a distant between the detecting control element and the control driving element to determine whether the contain lid is in a close state or open state with respect to the container body.

In one embodiment, the container lid comprises a ring shape shell arranged to be mounted on top of the container body and a cover panel pivotally connected to the ring shape shell for closing a lid opening of the ring shape shell and the container opening of the container body, wherein the control circuit comprises two pairs of detecting control element and control driving element, wherein the two detecting control elements are installed on the ring shape shell and the two control driving elements are installed on the container body and the cover panel respectively, such that when one of the detecting control elements leaves the corresponding control driving element while either the cover panel or the ring shape shell is opened with respect to the container body, the control circuit controls the dual-band ultraviolet lamp tube to turn off to stop generating the ultraviolet light rays, and that when both the ring shape shell and the cover panel are closed in place with respect to the container body, the detecting control elements detect an approaching of the corresponding control driving element and the control circuit controls the dual-band ultraviolet lamp tube to turn on to generate the ultraviolet light rays.

In one embodiment, a dual-band cold cathode ultraviolet lamp can be used in the waste container to produce 254 nm wavelength and 185 nm wavelength ultraviolet light rays at the same time, wherein the 254 nm wavelength has a higher photon energy for irradiating microorganisms for sterilization, and the 185 nm wavelength light wave irradiates the air to convert O2 (oxygen) into O3 (ozone) in the air for ozone sterilization. The dispersion of ozone can just make up for the shortcomings of ultraviolet rays that only propagate along a straight line and is disinfection with dead angles, so that it is more practical and effective to apply both means. In addition, a dual-band cold cathode ultraviolet lamp utilized in the present invention can provide ultraviolet sterilization and ozone sterilization at the same time, so that the circuit structure and mechanical structure of the present invention are also simplified while its cost is effectively reduced.

In one embodiment, due to the high driving voltage of the cold cathode ultraviolet lamp, it needs to be equipped with a boost driving circuit, wherein the boost driving circuit has high-voltage pulses and harmonics. Because the induction waste container should have the function of being induced to open the lid at any time to meet the needs of users, the infrared pulse testing circuit is required to continuously emit infrared detection pulses, and the sterilization and deodorization circuit of the cold cathode ultraviolet lamp needs to work continuously for a period of time to achieve better results. Therefore, when the cold cathode ultraviolet lamp is installed in the induction waste container, its high-voltage pulse and harmonic will have a strong interference with the infrared pulse testing circuit with weak signal processing in the induction circuit, and the infrared pulse testing circuit works unreliable during the time period of common operation, resulting in the induction waste container cannot be inductively opened at any time, that significantly affects the use demand thereof.

In accordance with another aspect of the invention, the present invention provides a sterilization and deodorization method of a waste container, comprising steps of:

(a) turning on a dual-band ultraviolet lamp tube, sealed in an isolation chamber provided below a container lid of the waste container, to generate ultraviolet light rays, including a direct sterilization ultraviolet light wave having a wavelength between 240 nm to 280 nm and an ozone sterilization ultraviolet light wave having a wavelength between 165 nm to 200 nm, propagating through a light-transmitting window of the isolation chamber into an inner cavity of the waste container, while the container lid is in a close state with respect to the container body; and (b) turning off the dual-band ultraviolet lamp tube to stop generating the ultraviolet light rays while the inner cavity of the container body is accessible to outside.

In one embodiment, in the step (b), the inner cavity of the container body is accessible to outside when the container lid is opened with respect to the container body.

In one embodiment, in the step (b), the inner cavity of the container is accessible to outside when the ring shape shell is separated from the container body.

Accordingly, the invention includes the following distinctive features:

1) By means of the isolation chamber provided to isolate with outside air, the dual-band ultraviolet lamp tube is sealingly contained between the reflector housing and the sealedly connected transparent quartz glass. Therefore, the glass surface may merely be wiped while it is dirty and the harsh environment in the waste container is prevented to affect the ultraviolet lamp tube in the isolation chamber, that optimizes the operating environment of the ultraviolet lamp tube, improves the service life span thereof and reduces the cost of use.
2) The transparent quartz glass is capable of enhancing a light transmittance of the ultraviolet light. The reflector housing can reflect most of the other ultraviolet light rays in the isolation chamber to penetrate through the transparent quartz glass into the container body, that greatly increases the intensity and number of effective light waves, and solves the conventional problems of light transmission and irradiation of the ultraviolet lamp tube.
3) The dual-band ultraviolet lamp tube provides double sterilizations, direct sterilization and ozone sterilization, wherein the ultraviolet light wave for direct sterilization has high photon energy to penetrate the cell membrane and nucleus of microorganisms, destroy the molecular bonds of their DNA, and kill them by making them lose replication ability or activity, and the ultraviolet light wave for ozone sterilization can turn O2 (oxygen) in the air into O3 (ozone) which has a strong oxidation effect that can diffuse in the container body and effectively kill bacteria. Ozone dispersion characteristics can just make up for the shortcomings of the ultraviolet for direct sterilization, including it only propagates along the straight line and the disinfection has dead angles. The two types of sterilization ultraviolet wave can sufficiently and effectively disinfect and sterilize the interior of the waste container, greatly improving the sterilization effect. In addition, during the disinfection and oxidation process, excess ozone will combine to become oxygen within 30 min to avoid ozone pollution.
4) The arrangement of the isolation chamber provides an excel environment for ozone sterilization of the ultraviolet light wave for ozone sterilization: Since ozone is highly corrosive, under the arrangement of the isolation chamber, ozone can only be diffused in the isolation chamber and the inner cavity of the container body, without affecting the electric circuit components and mechanical components within the interior space of the container lid.

In particular, the invention can further be embodied as follows:

The reflector housing is either a plastic electroplated member, or a resin shell body with a reflective film formed on inner side surfaces thereof, or a stainless steel made metal member with reflective arrangement on inner side surfaces thereof.

The reflector housing is preferred to be made of materials that are not easy to age, not easy to be corroded and oxidized, to avoid ozone corrosion and improve the reflection effect of light waves.

The ultraviolet light wave for direct sterilization is 240-280 nm ultraviolet light wave, preferably an ultraviolet light wave with a wavelength of 254 nm for direct sterilization.

The ultraviolet light wave for direct sterilization is also known as short-wave sterilization ultraviolet (UVC). The 253.7-254 nm wavelength ultraviolet light has the strongest photon energy and the best sterilization effect.

The ultraviolet light wave for ozone sterilization is 165-200 nm ultraviolet light wave, preferably an ultraviolet light wave with a wavelength of 185 nm for ozone sterilization.

The ultraviolet light wave (part of the UVD light wave) for ozone sterilization irradiated in the air can turn O2 (oxygen) in the air into O3 (ozone), wherein the 185 nm ozone sterilization ultraviolet light wave is the band with better effect.

The sealing silicone ring is a sealing ring having a cross-sectional inverted U-shape, such that a peripheral edge portion of the transparent quartz glass is positioned in an inner cavity of the U-shaped sealing ring, whereby the peripheral edge portion of the transparent quartz glass is completely covered in the sealing silicone ring.

The configuration of completely covering the peripheral edge of the transparent quartz glass can reduce damage caused by vibrations of the transparent quartz glass due to the vibration of the isolation chamber installed below the container lid while being flipped up and down frequently, so as to ensure the reliability of the structure. In addition, silicone can also prevent aging caused by ultraviolet radiation.

The control switch, which is either a Hall sensor, or an angle sensor, or a position limiting switch, comprises a control driving element and a detecting control element arranged in a separable manner, the control driving element being connected to the dual-band ultraviolet lamp tube and the control circuit.

For example, the control driving element of the angle sensor can be installed on a main rotating shaft of the container lid. When the container lid (or cover panel while the container lid is composed of a cover panel and a ring shape shell) opens at a certain angle (that is, when the container lid or cover panel is flipped up to open), the control circuit cuts off a power supply to the ultraviolet lamp tube while receiving a signal of the angle sensor and turns it off. When the container lid (or cover panel) is flipped down to close to a predetermined angle (when the container lid or cover panel is fully closed), the ultraviolet lamp tube is controlled to turn on for sterilization. For example, while the Hall sensor includes a Hall element as the control driving element and a magnet as the detecting control element, the ultraviolet lamp tube is turned off when the magnet leaves the detection range of the Hall element (i.e. when the container lid or cover panel is flipped up to open), and the ultraviolet lamp tube is turned on when the magnet enters the detection range of the Hall element (when the container lid or cover panel is flipped down to close). Accordingly, when the container lid or cover panel is opened, the control switch sends a signal and the control circuit controls the dual-band ultraviolet lamp tube to turn off to avoid ultraviolet from hurting human skin and eyes, and when the container lid or cover is closed, the control switch sends a signal to make the control circuit to timely turn on the ultraviolet lamp tube to sterilize the interior of the contain body in time.

One side of the container lid is pivotally connected with the container body, and a case is arranged at a hinging side of the container lid for receiving the control circuit. The case has a cavity provided therein and the insolation chamber is provided in the cavity. The control driving element and the detecting control element of the control switch are installed on the container lid and the container body respectively.

When the container lid and the container body are embodied as an inseparable connection structure, the isolation chamber is being flipped up and down with the container lid, so that the control switch is preferred to be installed on a side of the container lid or an open edge thereof.

The container lid comprises a ring shape shell and a cover panel. A side edge of the cover panel is hinged with the ring shape shell. The ring shape shell is sleeved to the container body, wherein a control circuit is installed in an inner cavity of the ring shall shell and the isolation chamber is arranged in a cavity provided in the ring shape shell.

The control switch includes two sets, the control driving element and the detecting control element of one of the two sets are installed on the ring shape shell and the container body respectively, and the control driving element and the detecting control element of another set are installed on the cover panel and the ring shape shell respectively.

In normal use, the control switch can be triggered by flipping the cover panel up or down. When it is necessary to detach the ring shape shell from the container body, the control switch can also be triggered, so as to effectively avoid harmful to the human body caused by ultraviolet leakage.

In view of above, the invention provides a sterilization and deodorization waste container with dual-band ultraviolet lamp tube, which utilizes an isolation chamber with the reflector housing and the transparent quartz glass to install the dual-band ultraviolet lamp tube, that effectively improves the operating environment of the ultraviolet lamp tube while avoiding influence on the internal circuit and mechanical components outside the isolation chamber, improves the service life span and reduces the cost of use. The drawbacks of light transmission and irradiation of ultraviolet lamp tube are resolved. The double ultraviolet sterilizations can substantially and effectively disinfect and sterilize the waste container that greatly improves the sterilization effect.

In accordance with another aspect of the invention, the present invention is embodied that, the ultraviolet lamp is a cold cathode ultraviolet lamp and the waste container is an induction waste container, and provides a control method of the induction waste container with cold cathode ultraviolet lamp sterilization and deodorization by means of a control circuit which comprise an infrared pulse testing circuit, an microcomputer controller, an ultraviolet sterilization and deodorization circuit of a cold cathode ultraviolet lamp, and a lid driving circuit, wherein the infrared pulse testing circuit, the sterilization and deodorization circuit and the lid driving circuit are all connected with a microcomputer controller, wherein the control method includes steps of:

S1: setting a working cycle and a turn-off cycle of the ultraviolet sterilization and deodorization circuit, wherein the working cycle is greater than 9 minutes, and setting the infrared pulse testing circuit to work n times per second in the working cycle of the ultraviolet sterilization and deodorization circuit, wherein each the working time of the infrared pulse testing circuit is 1 ms~8 ms, wherein a time between two adjacent operations of the infrared pulse testing circuit is a time interval;

S2: when the lid is closed and standby, entering a working state by the ultraviolet sterilization and deodorization circuit, and starting to time the working cycle;

S3: after the time interval, sending a trigger signal from the microcomputer controller to make the ultraviolet sterilization and deodorization circuit in a temporary turn-off state, and, during the temporary turn-off state, triggering the infrared pulse testing circuit by the microcomputer controller to start working and emitting infrared detection pulses by the infrared pulse testing circuit;

S4: when the infrared pulse testing circuit is working, if there is no object approaching the induction waste container, turning off the infrared pulse testing circuit after the working time of the infrared pulse testing circuit is ended, and then controlling the ultraviolet sterilization and deodorization circuit to start by the microcomputer controller, wherein the step S3 is returned until the working cycle of the ultraviolet sterilization and deodorization circuit is ended; and S5: turning off the ultraviolet sterilization and deodorization circuit, starting to time the turn-off cycle, and returning to the step S2 after the turn-off cycle ends.

Accordingly, the infrared pulse testing circuit emits infrared detection pulses during its working time, and the ultraviolet sterilization and deodorization circuit is temporarily closed for 1 ms~8 ms time. Taking an one-second cycle as an example, the infrared pulse testing circuit emits infrared detection pulses 3 times in each one-second cycle, and the ultraviolet sterilization and deodorization circuit is temporarily closed for a time of 1 ms each time, in which a working time ratio of the ultraviolet sterilization and deodorization circuit is 99.7% through computation; if the infrared pulse testing circuit emits infrared detection pulses 8 times in each one-second cycle and the ultraviolet sterilization and deodorization circuit is temporarily turned off for 8 ms, the working time ratio of the ultraviolet sterilization and deodorization circuit is 93.6% through computation. Such high working time ratio is equivalent to that the sterilization and deodorization circuit of the cold cathode ultraviolet lamp is almost in a continuous working state, which basically does not affect a continuity of ultraviolet irradiation and a change of ozone concentration.

The working time of the present invention based on the infrared pulse testing circuit is much smaller than the working time of the cold cathode ultraviolet lamp sterilization and deodorization circuit, while the ultraviolet sterilization and deodorization circuit adopts a predetermined number of temporary turn-off for extremely short time, such that the two working times thereof are being embedded control, that is embedding the working time of the infrared pulse testing circuit in the working cycle of the ultraviolet sterilization and deodorization circuit, so as to effectively implement the separation and integration of time during the working state of the ultraviolet sterilization and deodorization circuit and the infrared pulse testing circuit. Therefore, on one hand, the ultraviolet sterilization and deodorization circuit will not interfere with the infrared pulse testing circuit to ensure the working stability of infrared pulse testing circuit and the reliability of the induction opening of the lid; on the other hand, the ultraviolet sterilization and deodorization circuit is basically maintained in a continuous working state during working hours that ensures the continuity of ultraviolet irradiation, so that the ultraviolet sterilization time and the accumulation requirements of ozone concentration can be satisfied. In addition, the ultraviolet sterilization and deodorization circuit is set with a turn-off cycle, which can effectively extend the service life of the ultraviolet lamp and can effectively control the ozone concentration in the waste container.

The present invention may be further specified as:

The number of infrared detection pulses emitted by the infrared pulse testing circuit in the working cycle of the ultraviolet sterilization and deodorization circuit is 3~8 times per second, and the working time ratio of the ultraviolet sterilization and deodorization circuit is greater than 93.6%.

Regarding the ensuring of the infrared induction opening of the lid, the working time of the ultraviolet sterilization and deodorization circuit is ensured to have a high working time ratio, so as to ensure the continuity of ultraviolet irradiation and the accumulation of ozone concentration.

During the ultraviolet sterilization and deodorization circuit is in its working cycle, when the infrared pulse testing circuit works, such as an approaching object is detected through the emitted infrared detection pulse(s), the infrared detection pulse(s) is reflected by a surface of the object, and then the infrared pulse testing circuit processes the reflected signal from the object and feeding back to a microcomputer controller. The microcomputer controller controls the ultraviolet sterilization and deodorization circuit being maintained in the turn-off state, such that the working cycle temporarily stops timing, the microcomputer controller further triggers the lid driving circuit, and the container lid is opened under the control of the lid driving circuit. After the container lid is closed, the working cycle continues to time.

Because it only takes a few seconds from the induction trigger to open the lid of the induction waste container and to close the container lid after disposal of the waste in the induction waste container, the ultraviolet sterilization and deodorization circuit returns to its original working state after closing the lid and continues the accumulation of the working cycle, that can not only ensure the integrity of the working cycle, but also basically will not affect the overall sterilization and deodorization effect while ensuring the induction opening of the lid being convenient to use.

During the ultraviolet sterilization and deodorization circuit is in a turn-off state of the turn-off cycle, if an approaching object is detected through the emitted infrared detection pulse(s), the infrared detection pulse(s) is reflected by a surface of the object, and then the infrared pulse testing circuit processes the reflected signal from the object and feeding back to a microcomputer controller. Then, the turn-off cycle temporarily stops timing and the microcomputer controller further triggers the lid driving circuit to open the container lid under a control by the lid driving circuit. After the container lid is closed, the turn-off cycle in the microcomputer controller continues timing.

Likewise, the short opening and closing of the lid will not affect the integrity of the turn-off cycle. On the other hand, because ozone is an unstable gas, having a semi-decay phase, a fixed length of the turn-off cycle can be timely started after ozone is consumed to a certain extent to ensure the sterilization and deodorization effect.

The working cycle is 10~30 minutes, and the turn-off cycle is 20~60 minutes.

In order to ensure the sterilization and deodorization effect, the present invention takes a predetermined amount of time for ultraviolet irradiation to kill bacteria, and the concentration of ozone also needs a predetermined amount of time to accumulate, so that the ultraviolet sterilization and deodorization circuit is preferred to continue to work for more than 10 minutes. Considering the rate of bacterial growth and ozone consumption, the turn-off cycle should be less than 60 minutes.

In view of above, the present invention provides a circuit control method of induction waste container with cold cathode ultraviolet lamp sterilization and deodorization, which embeds the working time of the infrared pulse testing circuit into the working time of the ultraviolet sterilization and deodorization circuit, so as to effectively implement the separation and integration of time during the working state of the ultraviolet sterilization and deodorization circuit and the infrared pulse testing circuit, avoid the interference of the ultraviolet sterilization and deodorization circuit with respect to the infrared test circuit, accomplish that the lid can be opened inductively at any time in the standby state, prolong the service life of the cold cathode ultraviolet lamp, control the ozone concentration in the waste container, and achieve a more ideal sterilization and deodorization effect simultaneously. The present invention has good safety performance, simple and reliable circuit structure, low cost, and strong practical application value.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
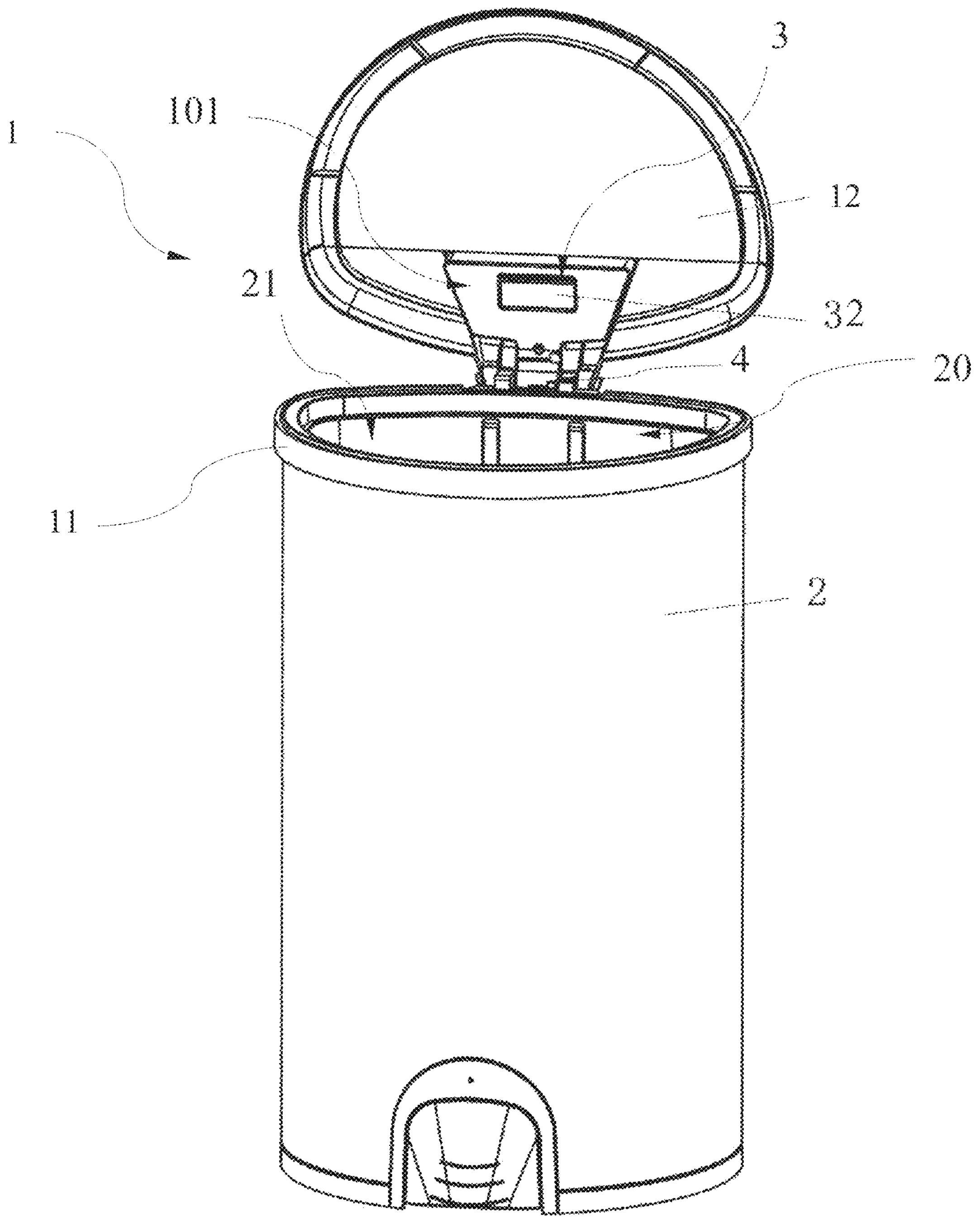
FIG. 1 is a structural perspective view of a sterilization and deodorization waste container having dual-band ultraviolet lamp tube according to a first preferred embodiment of the invention.
Figure 2:
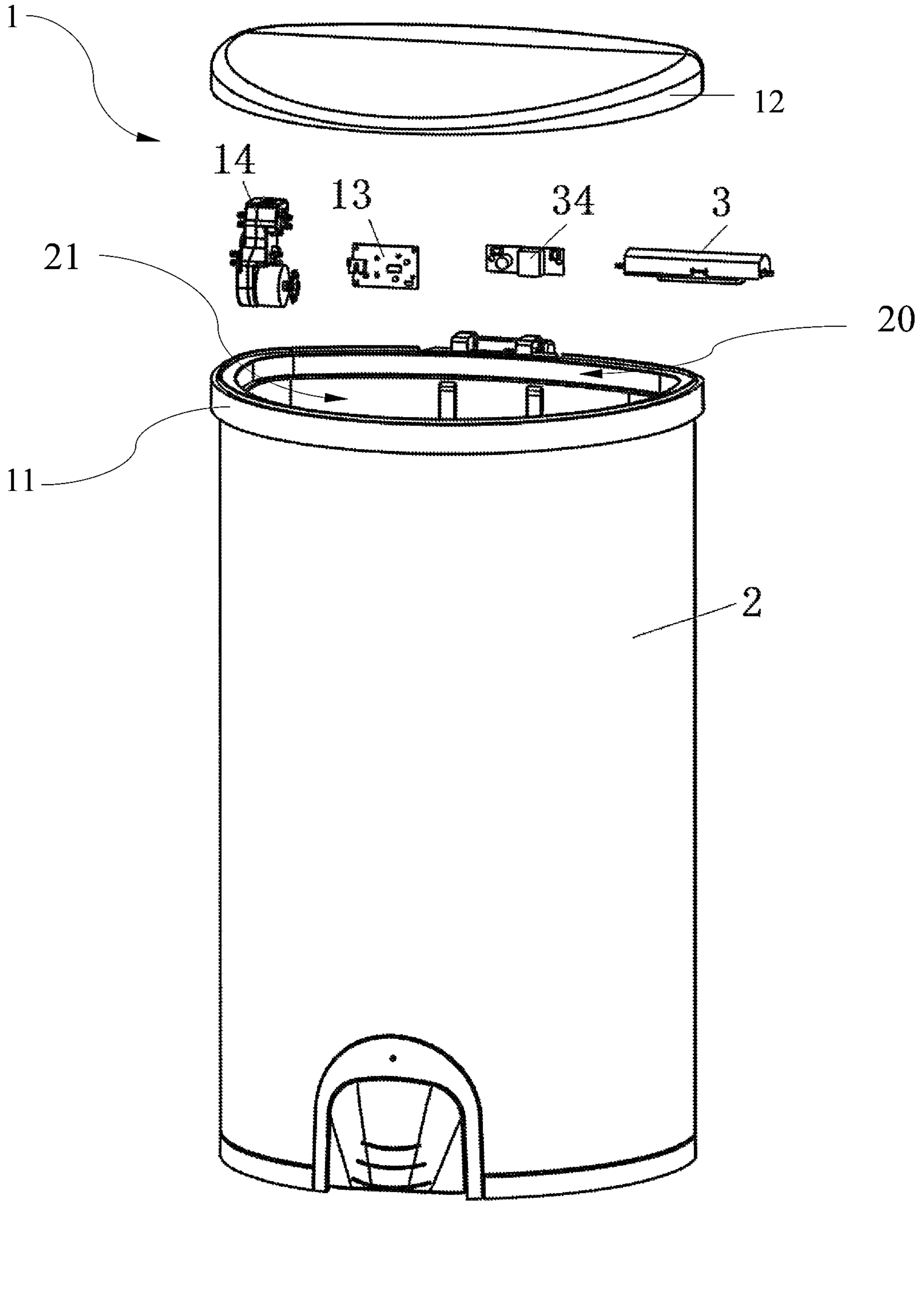
FIG. 2 is an exploded structural perspective view of the sterilization and deodorization waste container as shown in FIG. 1.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Referring to FIG. 1 to FIG. 19, the invention discloses a dual-band ultraviolet sterilization and deodorization arrangement which is adapted to be utilized in various types of waste container, such as a waste container with its lid pivotally connected to its container body as described in a first preferred embodiment hereinafter referencing FIG. 1 to FIG. 5, and an induction waste container comprising a container lid comprising a ring shape shell configured to be mounted on the container body and a cover panel or lid pivotally connected to the ring shape shell as described in a second preferred embodiment hereinafter referencing FIG. 6 to FIG. 16. For ease of understanding, the elements of the dual-band ultraviolet sterilization and deodorization arrangement in both the first and second preferred embodiments are described with the same reference numbers correspondingly.

First Preferred Embodiment

This embodiment is a sterilization and deodorization waste container having dual-band ultraviolet lamp tube, while its container lid is not separable from its container body (such as foot-step waste container, foot-touch waste container, and etc., the present embodiment referring to the foot-touch waste container), the configurations of the foot touch control and the opening and closing operation of the container lid are conventional art that is not repeatedly described in the first preferred embodiment.

Referring to FIG. 1 to FIG. 5, a sterilization and deodorization waste container having a dual-band ultraviolet lamp tube includes a container lid 1, a container body 2 and a control circuit 13. The container body 2 has an inner cavity 21 adapted for storing waste and a container opening 20 communicating the inner cavity 21 with outside. The container lid 1 comprises a circular housing 11 provided at a top edge of the container body 2 and a lid 12 pivotally connected to the circular housing 11, such that the lid 12 is pivotally couple at a container opening 20 above the container body 2 to be moved selectively between an open state to expose the inner cavity 21 to outside through the container opening 20 and a close state to cover the container opening 20 and close the inner cavity 21 from outside.

According to the first preferred embodiment, the circular housing 11 is a ring shape member mounted on the top edge of the container body 2 and the lid 12 is hinged to the container opening 20 in the top of the container body 2.

The control circuit 13 and a lid opening and closing driving device 14 are disposed on the container body 2. An isolation chamber 3, which is a housing having an isolation cavity 30 defined therein, isolated from the air outside is arranged below the container lid 1.

A light-transmitting widow 32 is formed below the isolation chamber 3. Due to the harsh environment of the waste container, the dual-band ultraviolet lamp tube 33 is a U-shaped dual-band ultraviolet tube and arranged in the isolation cavity 30 of the air-isolated isolation chamber 3. Because of the low penetrability of ultraviolet light, the light-transmitting widow 32 previous to light of the isolation chamber 3 needs to be made of transparent quartz glass with extremely high light transmittance.

In other words, since the ultraviolet light penetration ability is extremely weak, a transparent quartz glass 32 having very high light transmittance is embodied as the light-transmitting window 32 of the isolation chamber 3.

The dual-band ultraviolet lamp tube 33 generates ultraviolet light rays, with 254 nm wavelength and 185 nm wavelength, irradiated into the waste container through the light-transmitting window 32 made of the transparent quartz glass, so as to use the ultraviolet light rays for sterilization and deodorization. In which, the ultraviolet light wave with 254 nm wavelength (also known as short-wave sterilization ultraviolet) has a higher photon energy, that can penetrate cell membranes and nucleus of microorganisms, destroy the molecular bonds of their DNA, and make them losing replication ability or activity and die while irradiating microorganisms. Also, the irradiating of the ultraviolet light wave with 185 nm wavelength in the air can turn $O_2$ (oxygen) in the air into $O_3$ (ozone). Ozone, which has a strong oxidation effect, can effectively kill bacteria. The diffusion and dispersion ability of ozone fitly make up for the shortcoming of ultraviolet that only propagates along a straight line and has dead angles and corners for disinfection, such that the function of sterilization and deodorization is strengthened.

Since the container lid 1 is mounted on the container body 2, the isolation chamber 3 is preferred to be positioned at or above the container opening 20 in such a manner that the ultraviolet light rays generated by the dual-band ultraviolet lamp tube 33 irradiated all positions in the inner cavity 21 of the container body 2 through the light-transmitting window 32.

According to the first preferred embodiment, the isolation chamber 3 comprises a reflector housing 31, the transparent quartz glass 32 and a sealing silicone ring 321. A peripheral edge portion of the transparent quartz glass 32 is affixed with the sealing silicone ring 321 which has a "U" shaped cross section to protect. The dual-band ultraviolet lamp tube 33 is arranged in the sealed isolation chamber 3 formed by the reflector housing 31 and the transparent quartz glass 32. Since ultraviolet has a strong aging ability and ozone is very corrosive, the dual-band ultraviolet lamp tube 33 is enclosed in the sealed isolation chamber 3, so that the ultraviolet light rays are prevented from being irradiated onto plastic structural members of a drive control mechanism and are concentrated onto the waste stored in the waste container, and the ozone generated by irradiation of the ultraviolet light rays will not be diffused into the internal space of the container lid 1, which may otherwise corrode and oxidize the control circuit 13 and the internal structural components.

In other words, on one hand, the ultraviolet light wave avoids irradiating plastic structural components of the driving control mechanism but concentrates in positions of the waste contained in the container body 2 and, on the other hand, the ozone generated by the ultraviolet light wave irradiation does not be dispersed into an inner space of the container lid 1, causing the control circuit 13 and the internal structural components to be corroded and oxidized by the ozone.

At the same time, the dual-band ultraviolet lamp tube 33 is isolated and protected from being stained and polluted. If the light-transmitting window 32 is stained, only the transparent quartz glass (light-transmitting window) 32 needs to be wiped, and sufficient ultraviolet light wave irradiation is guaranteed.

The reflector housing 31 may be a plastic electroplated part, a reflective film, a stainless steel metal part, or a part made of other materials not prone to aging, corrosion and oxidization, and can reflect ultraviolet light rays with the wavelength of 254 nm and the wavelength of 185 nm, for example, so that most ultraviolet light can be irradiated int to the waste container for sterilization and generate ozone in the waste container for sterilization and deodorization.

In other words, the reflector housing 31 (the reflector housing 31 may be made of materials such as electroplated plastic member, a reflective filmed or a stainless steel made metal member and other materials that are not easy to age, not easy to be corroded and oxidized, the reflector housing 31 in the present embodiment referring to an electroplated plastic member) is configured to reflect ultraviolet light rays into the inner cavity 21 of the container body 2 of the waste container, which greatly increases the effective light wave intensity. The ultraviolet light rays reflected through the reflector housing 31 can only be irradiated into the waste container through the transparent quartz glass 32. The transparent quartz glass 32 is capable of transmitting most of the ultraviolet light rays with 254 nm wavelength and 185 nm wavelength, that ensures most of the ultraviolet light rays being irradiated into the waste container for sterilization and generating ozone for sterilization and deodorization in the waste container.

In addition, since silicone has strong anti-aging ability, the scaling silicone ring 321 of the present embodiment adopts a sealing silicone with a "U" shaped cross-section.

According to the first preferred embodiment, the container lid 1 is configured to be inseparable from the container body 2. A control switch 131 is mounted on the container body 2 (the control switch 131 may be a Hall element, a position limiting switch, an angle sensor and etc.) According to the first preferred embodiment, the control switch 131 is embodied as a Hall element 131). A magnet 132 is mounted on the container lid 1 and, when the container lid 1 is opened, the magnet 132 leaves the measurement range of the Hall element 131 along with the container lid 1. After the control circuit 13 receives a signal from the Hall element 131, the ultraviolet tube driving circuit 34 to light off to stop generating ultraviolet light to protect the skin and eyes of users against harm. Only when the container lid 1 is closed in place and the Hall element 131 detects that the magnet 132 is approaching, the control circuit 13 will control the dural-band ultraviolet lamp tube 33 to light up, otherwise, the dural-band ultraviolet lamp tube 33 will be kept off all the time.

Figure 5:
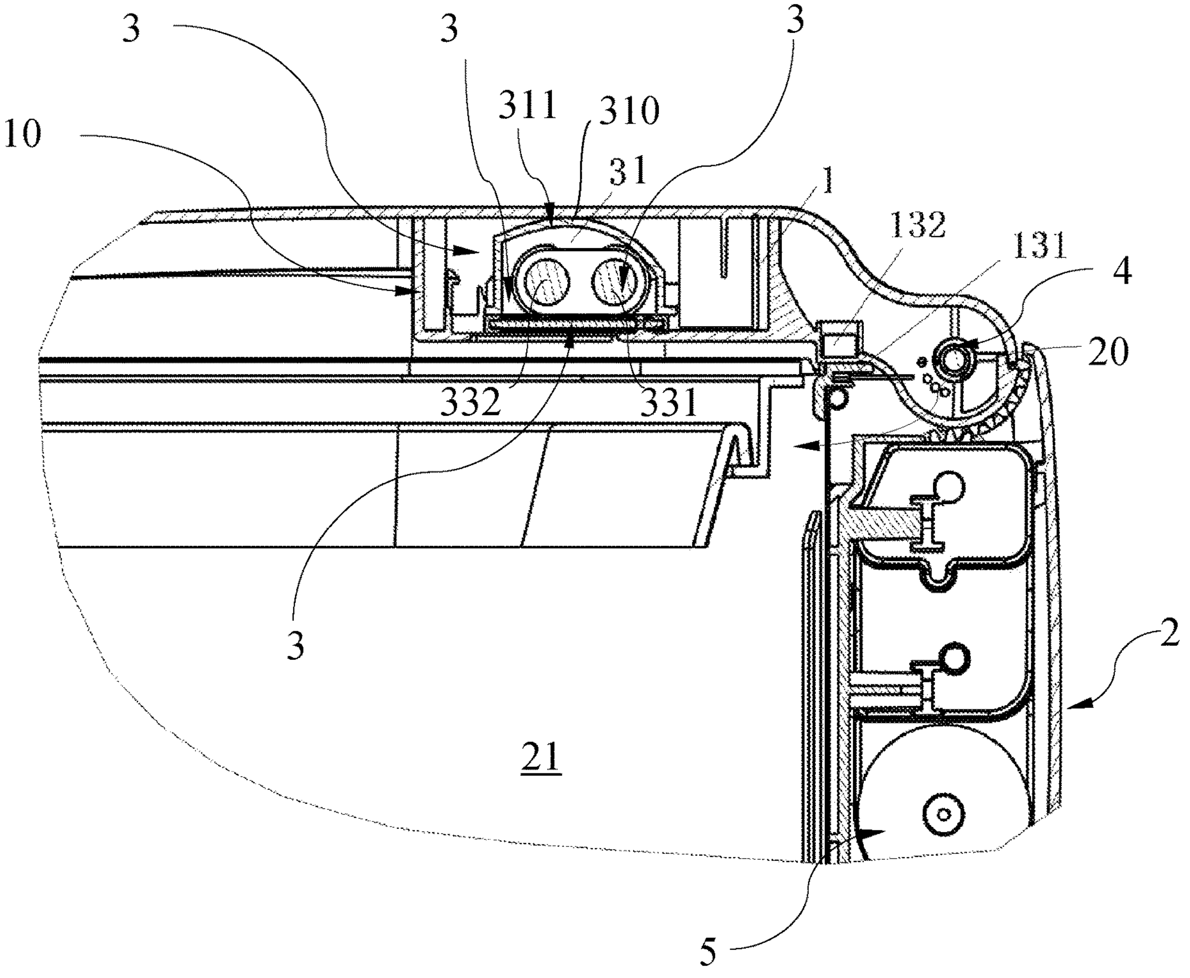
FIG. 5 is a partial structural sectional view of the sterilization and deodorization waste container with the dual-band ultraviolet lamp tube as shown in FIG. 1 according to the first preferred embodiment of the invention.
Figure 6:
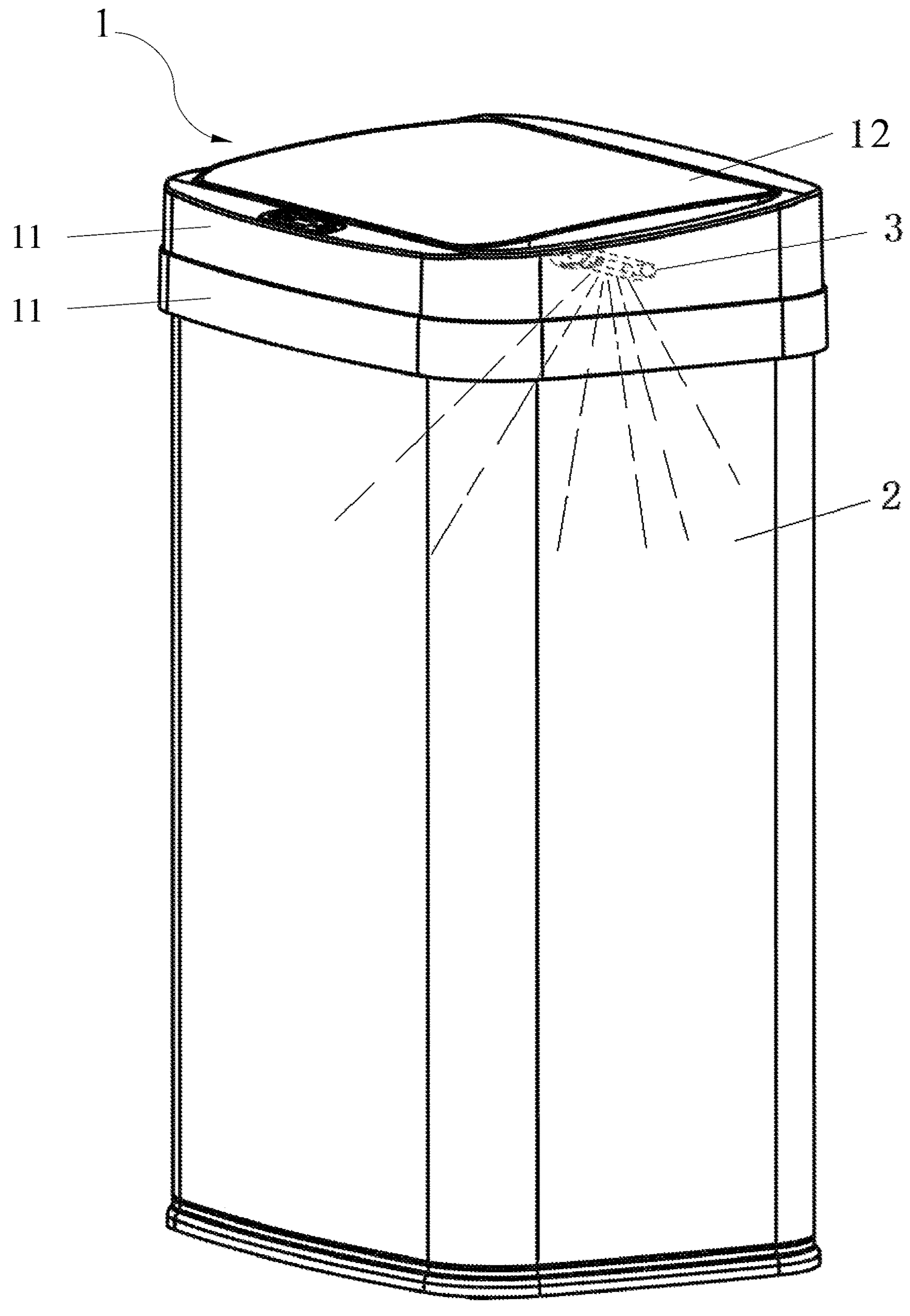
FIG. 6 is a perspective view of the sterilization and deodorization waste container with the dual-band ultraviolet lamp tube according to a second preferred embodiment of the invention.
Figure 7:
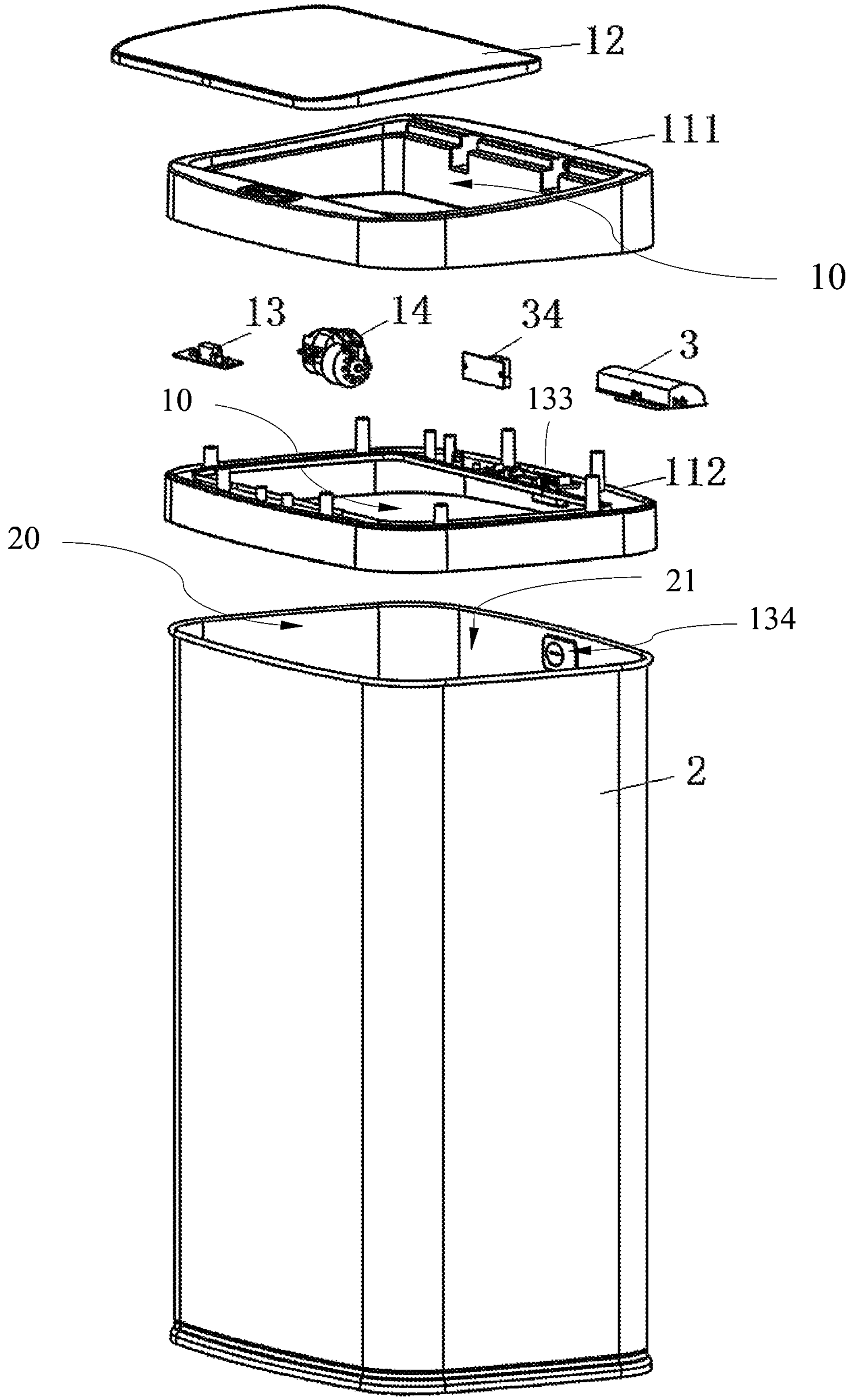
FIG. 7 an exploded structural perspective view of the sterilization and deodorization waste container as shown in FIG. 6.

In particular, according to the first preferred embodiment, as shown in FIG. 5, the magnet 132 is embodied as an actuator mounted on an underside of the lid 12 of the container lid 1 with respect to the Hall element (control switch) 131, which is mounted on the circular housing 11 of the container lid 1 correspondingly, such that when the lid 12 of the container lid 1 is flipped up to open (the magnet 132 leaves a detection range of the Hall element 131 with the circular housing 11 of the container lid 131, the control circuit 13 receives a signal sent from the Hall element 131, and the dual-band ultraviolet lamp tube 33 is turned off by a ultraviolet lamp tube driving circuit 34 to cease the generation of the ultraviolet light rays to prevent causing harm to human skin and eyes. When the lid 12 of the container lid 1 is flipped down to the circular housing 11 of the container lid 1 to close in place, the Hall element 131 detects an approaching of the magnet 132 and the control circuit 13 controls the dual-band ultraviolet lamp tube 33 to turn on, or otherwise, the dual-band ultraviolet lamp tube 33 is always remained in a turn-off state.

As shown in FIG. 5, the sterilization and deodorization waste container further comprises a DC power source 5, embodied as one or more batteries, for supplying electric power to the dual-band ultraviolet lamp tube 33, the control circuit 13, the ultraviolet lamp tube driving circuit 34, and the control switch 131 according to the first preferred embodiment of the present invention.

Second Preferred Embodiment

Referring to FIGS. 3-4 and 6-16, according to a second preferred embodiment of the present embodiment, the sterilization and deodorization waste container, embodied as an induction waste container, having dual-band ultraviolet lamp tube is illustrated, wherein its container lid is separable from its container body (such as induction waste container, the present embodiment referring to an induction waste container). The configurations of the infrared sensing component and the opening and closing operation of the container lid are conventional art as disclosed in prior patents, such as U.S. Pat. Nos. 6,812,655, 7,598,693, 7,750,591, 8,129,930, 8,547,049, 8,678,219, 10,526,139, 10,822,165, 10,928,796, 11,338,994, 11,390,458, 11,396,423, and 11,603,262.

Referring to FIGS. 3, 4 and 6-16, a sterilization and deodorization waste container with a dual-band ultraviolet lamp tube is illustrated, which includes a container lid 1, a container body 2 and a control circuit 13, the container body 2 being used to store waste.

The container lid 1 comprises a circular housing 11, which comprises a circular container head 111 and a circular middle seat 122, and a lid 12, wherein the lid 12 is hinged to the circular housing 11 and the container lid 1 is disposed at an opening 20 in the top of the container body 2. The control circuit 13 and a lid opening and closing driving device 14 are mounted in a cavity of the circular housing 11 formed after the circular container head 111 and the circular middle seat 112 are buckled together. An isolation chamber 3 isolated from air is formed below the container lid 1. A dual-band ultraviolet lamp tube 33 is disposed in the isolation chamber 3 and is made of transparent quartz glass 32 with extremely high light transmittance.

In particular, similar to the first preferred embodiment, the container body 2 has an inner cavity 21 for storing waste and defines a container opening 20 at a top end communicating the inner cavity 21 with outside. The container lid 1 is placed above a container opening 20 of the container body 2. The circular housing 11 of the container lid 1 according to the second preferred embodiment is embodied as a ring shape housing, wherein the circular container head 111 thereof is embodied as a ring shape shell and the circular middle seat 122 thereof is embodied as a ring shape retainer body 122. A receiving cavity 110 is defined in the ring shape housing 11 and a lid opening 10 is defined by the ring shape shell to communicate the container opening 20 so as to communicate the inner cavity 21 of the container body 2 with outside. The lid 12 is embodied as a lid panel 12 pivotally connected to the ring shape housing 11 to cover the lid opening 10 as well as the container opening 20.

Similarly to the first preferred embodiment, the sterilization and deodorization waste container according to the second preferred embodiment also comprises a lid opening and closing driving device 14, wherein the control circuit 13 and the lid opening and closing driving device 14 are installed in the receiving cavity 110 of the circular housing 11, defined after the ring shape shell 111 and the ring shape retainer body 112 are affixed together. The sterilization and deodorization waste container comprises an isolation chamber 33, having a light-transmitting window 32, isolated from the air outside and arranged below the container lid 1, wherein a dual-band ultraviolet lamp tube 3 is installed in the isolation chamber 33, and the light-transmitting window 32 is made of transparent quartz glass having very high light transmittance and provided below the dual-band ultraviolet lamp tube 33 and above the lid opening 10 and the container opening 20.

The dual-band ultraviolet lamp tube 33 generates ultraviolet light rays with a 254 nm wavelength and ultraviolet light rays with a wavelength of 185 nm, which irradiate into the waste container through the transparent quartz glass (light-transmitting window) 32 and the ultraviolet light rays are used for sterilization and deodorization, wherein the ultraviolet light rays with the wavelength of 185 nm generate ozone for sterilization and deodorization, and the ozone can be dispersed in the whole waste container by means of its dispersity to exactly make up the defects of liner propagation and sterilization dead corners of the ultraviolet light, so that the sterilization and deodorization function is enhanced.

In other words, due to the dispersion and diffusion ability of ozone, the ozone fills the interior space of the waste container, especially the inner cavity 21 of the container body 2, that fitly makes up for the shortcoming of ultraviolet that only propagates along a straight line and has dead angles and corners for disinfection, such that the function of sterilization and deodorization is strengthened.

The configurations and material selections of the isolation chamber 3, the reflector housing 31, the transparent quartz glass 32, the sealing silicone ring 321, the dual-band ultraviolet lamp tube 33 and the sterilization and deodorization principle of the dual-band ultraviolet lamp tube 33 may refer to the description in the first preferred embodiment and are not repeatedly described in this embodiment.

According to the second preferred embodiment, the container lid 1 may be separated from the container body 2. As mentioned above, the container lid 1 comprises the ring shape housing 11 and the lid 12, wherein a control switch is mounted on the container body 2 (the control switch may be a Hall element, a position limiting switch, an angle sensor, and etc., and in this embodiment, the control switch is a Hall element, namely a first Hall element 131 and a second Hall element 133). A second magnet 134 is mounted on the container body 2, and when the container lid 1 is separated from the container body 2, the magnet 134 leaves a detection range of the second Hall element 133. After the Hall element 133 generates a signal, the control circuit 13 controls the dual-band ultraviolet lamp tube 33 to turn off to stop generating the ultraviolet light rays to prevent causing harm to human skin and eyes. Similarly, a first magnet 132 is mounted on the lid 12; when the lid 12 is opened, the magnet 132 leaves a measurement range of the second Hall element 131 along the with the lid 132; after the first Hall element 131 generates a signal, the control circuit 13 controls the dual-band ultraviolet tube 33 to light off to stop generating ultraviolet light to protect the skin and eyes of users against harm. Only when the lid 12 is closed in place and is place on the container body 2, the control circuit 13 will control the dual-band ultraviolet lamp tube 33 to light up to work, otherwise, the control of the dual-band ultraviolet lamp tube 33 will be always in an off state. om this basis, the sterilization time of the dual-band ultraviolet lamp tube 33 can be set.

In other words, the lid 12 is equipped with the magnet 132 such that, when the lid 12 is opened, the magnet 132 leaves the detection range of the first Hall element 131. After the first Hall element 131 generates a signal, the control circuit 13 controls the dual-band ultraviolet lamp tube 33 to turn off to stop generating the ultraviolet light rays to prevent causing harm to human skin and eyes. When the lid 12 is closed in place and the container lid 1 is placed on the container body 2, that is only while these two conditions are met at the same time, the control circuit 13 controls the dual-band ultraviolet lamp tube 33 to turn on and operate, or otherwise, the dual-band Ultraviolet lamp tube 33 is always remained in the turn-off state. Based on the embodiments described above, the ultraviolet lamp tube 33 can also be set with a predetermined sterilization time period.

Figure 8:
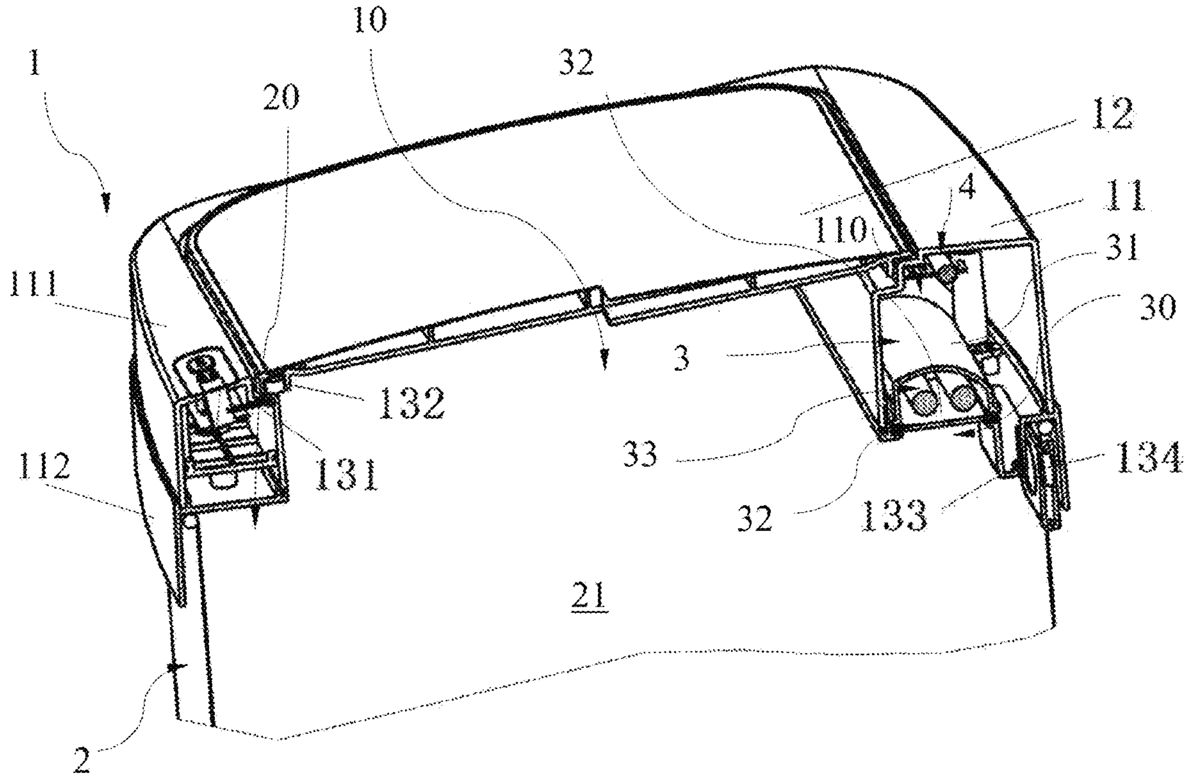
FIG. 8 is a partial structural sectional view of the sterilization and deodorization waste container with the dual-band ultraviolet lamp tube as shown in FIG. 6 according to the second preferred embodiment of the invention.
Figure 9:
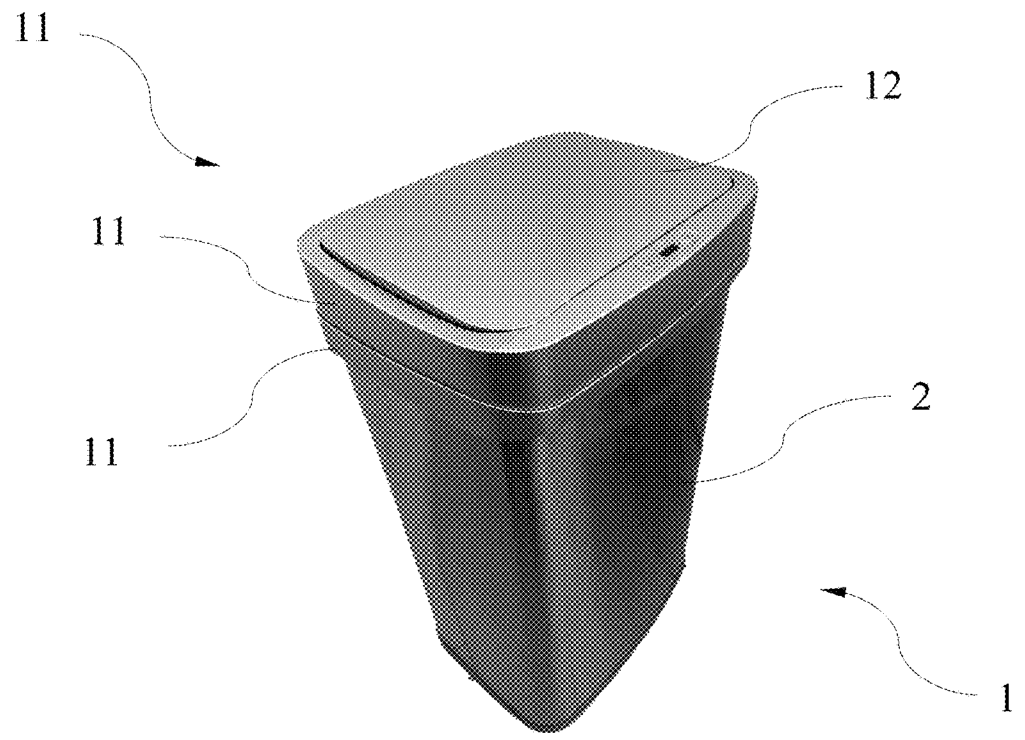
FIG. 9 is another perspective view of the sterilization and deodorization waste container, while the lid being in close state, according to the second preferred embodiment of the invention.
Figure 10:
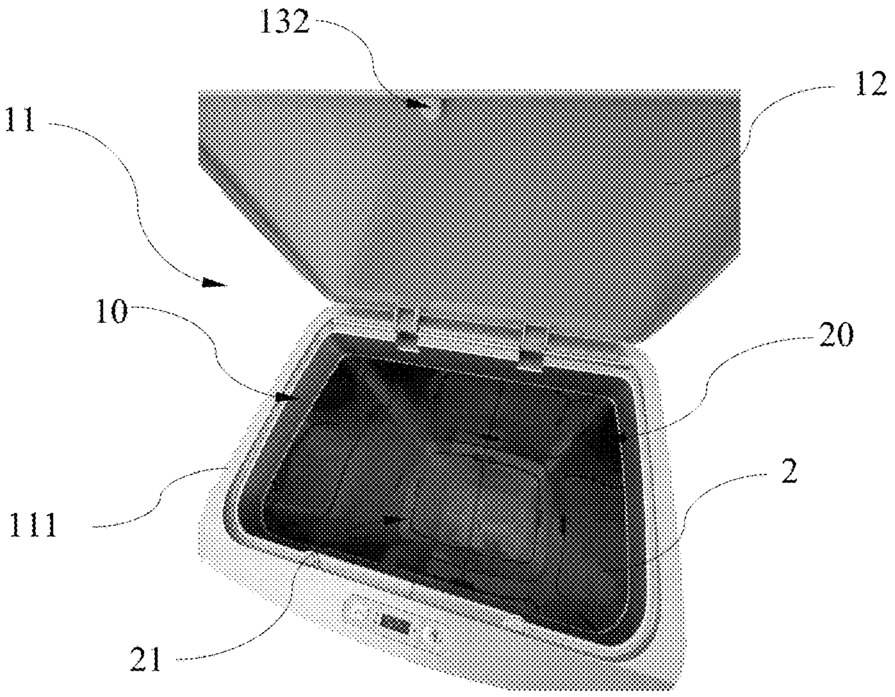
FIG. 10 is a top perspective view of the sterilization and deodorization waste container, while the lid being in open state, according to the second preferred embodiment of the invention.
Figure 11:
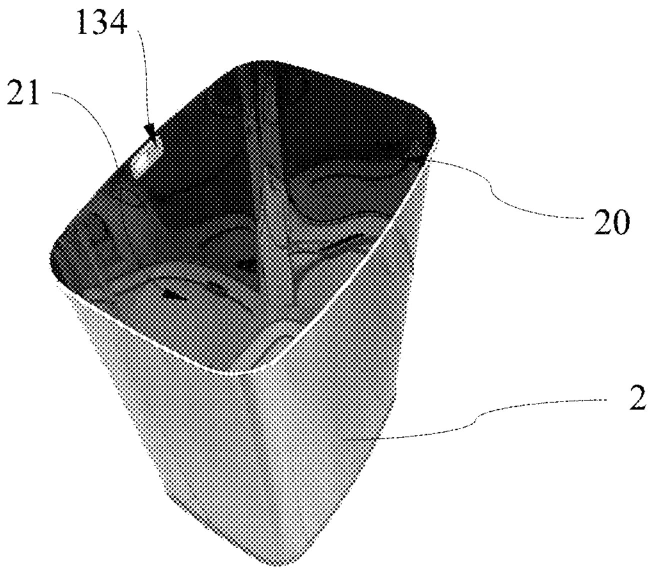
FIG. 11 is a perspective view of the container body of the sterilization and deodorization waste container according to the second preferred embodiment of the invention.
Figure 12:
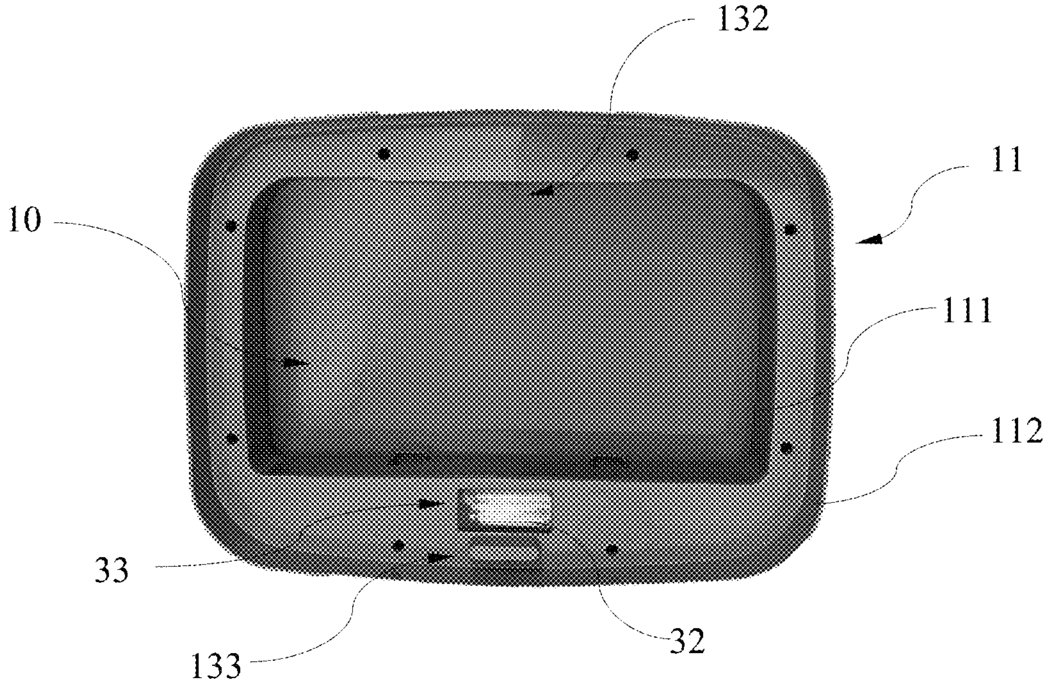
FIG. 12 is a bottom view of the container lid of the sterilization and deodorization waste container, while the lid being in close state, according to the second preferred embodiment of the invention.
Figure 13:
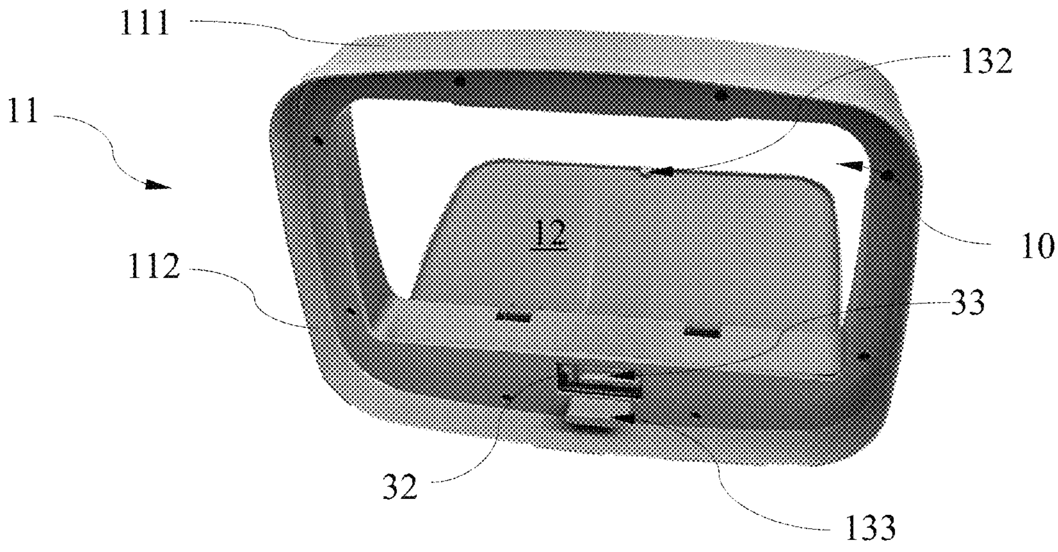
FIG. 13 is a bottom perspective view of the container lid of the sterilization and deodorization waste container, while the lid being in open state, according to the second preferred embodiment of the invention.

FIG. 9 to FIG. 16 are image views of the second preferred embodiment of the present invention. As shown in FIGS. 8, 10 and 13, the first magnet 131 is arranged at a bottom side of a front edge portion of the lid 12 while the first Hall element 131 (first control switch) is arranged at a corresponding position of a front edge portion of the ring shape shell 111 of the ring shape housing 11 of the container lid 1, such that when the lid 12 is flipped down to the close state (as shown in FIG. 8 and FIG. 9, the first magnet 131 is right on top of the first Hall element 131. As shown in FIGS. 7, 8 and 11-14, the second magnet 134 is arranged at a rear side of a top edge portion the container body 2 and the second Hall element (second control switch) 133 is downwardly extended from a corresponding rear portion of a bottom side of ring shape retainer body 112 of the ring shape housing 11 of the container lid 1, such that when the container lid 1 is mounted on top of the container body 2 (as shown in FIGS. 6, 8, 9, and 10) the second Hall element 133 is positioned adjacent to the second magnet 134. Accordingly, when the container lib 1 is mounted on the container body 2 in place and the lid 12 is in the close state to enclose the lid opening 10 and container opening 20, the first and second Hall elements 131, 133 and the first and second magnets 132, 134 are detected with each other respectively, and thus the control circuit 13 controls the dual-band ultraviolet lamp tube 33 to turn on and operate accordingly. However, either the first magnet 132 leaves the first Hall element (first control switch) 131 while flipping up the lid 12 to open the container opening 20, or the second magnet 134 leaves the second Hall element (second control switch) 133 while the container lid 1 is detached from the container body 2, the control circuit 13 controls the dual-band Ultraviolet lamp tube 33 to be always remained in the turn-off state.

Figure 14:
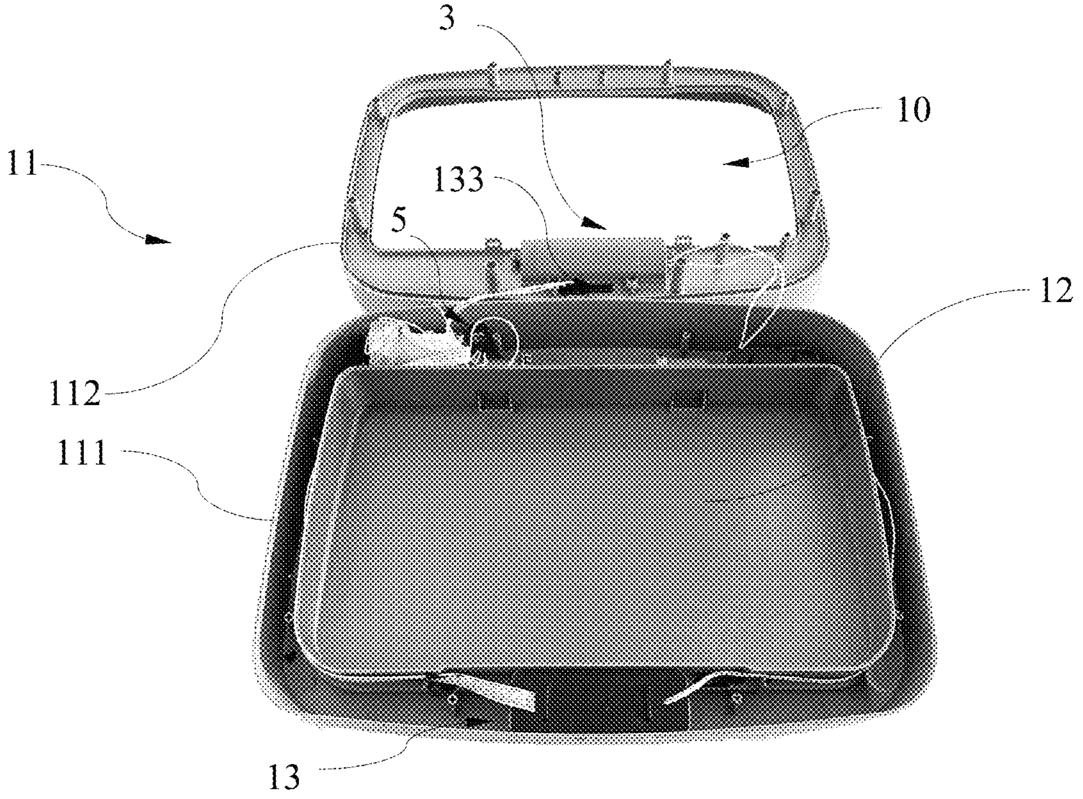
FIG. 14 is an exploded perspective view of the container lid of the sterilization and deodorization waste container according to the second preferred embodiment of the invention.

The As shown in FIG. 14, the sterilization and deodorization induction waste container further comprises a power source 5, which is embodied as an electrical power terminal for connecting with AC power source. In other embodiment, such as the first preferred embodiment, the power source 5 includes one or more batteries, for supplying electric power to the dual-band ultraviolet lamp tube 33, the control circuit 13, the ultraviolet lamp tube driving circuit 34, and the control switches 131, 133.

Figure 15:
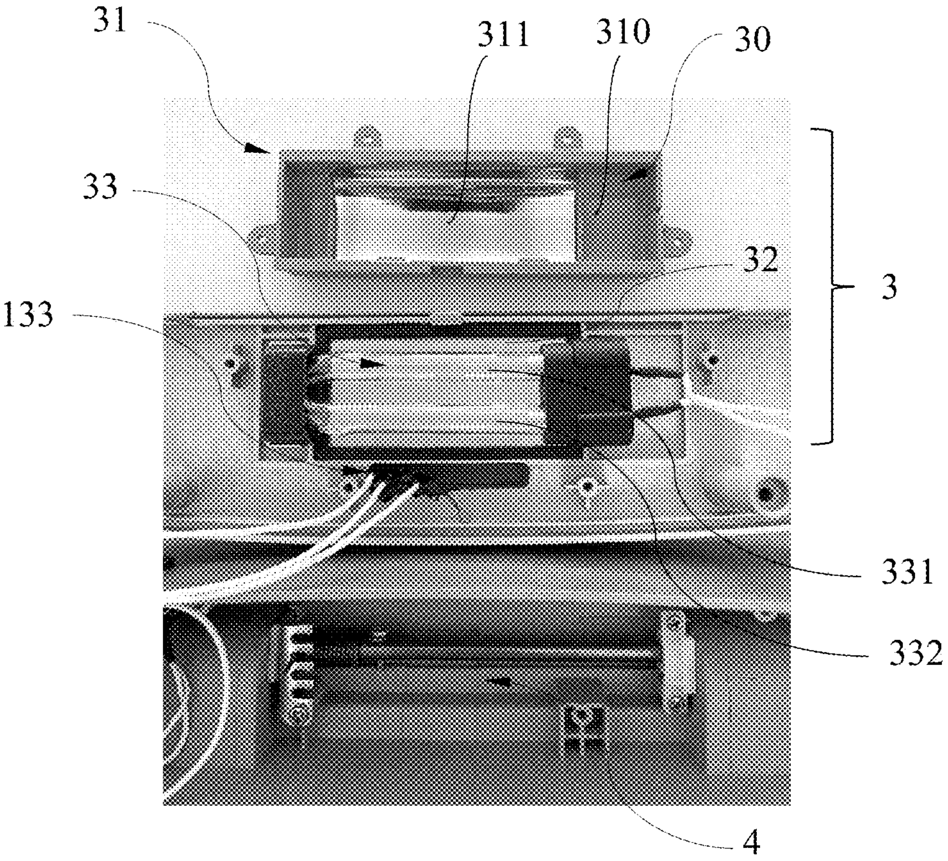
FIG. 15 is an exploded partial perspective view of the reflector housing and the isolation chamber of the sterilization and deodorization waste container according to the second preferred embodiment of the invention.

In view of the above first and second preferred embodiments, as shown in FIG. 1 to FIG. 16, the isolation chamber 3 comprises a reflector housing 31, wherein the light-transmitting window 32 which is a transparent quartz glass sealingly is mounted at an opening 30 of the reflector housing 31 (as shown in FIG. 8 and FIG. 15). The dual-band ultraviolet lamp tube 33 which is situated in the isolation chamber 3 and sealingly covered by the reflector housing 31 is electrically connected to the control circuit 13, such that the ultraviolet light rays generated from the dual-band ultraviolet lamp tube 33 radiate through the light-transmitting window 32 into the inner cavity 21 of the container body 2. In other words, the dual-band ultraviolet lamp tube 33 and the control circuit 13 are equipped with each other to form a dual-band ultraviolet sterilization and deodorization arrangement, arranged above the container opening 20 of the container body 2. It is appreciated that the dual-band ultraviolet sterilization and deodorization arrangement of the present invention can be configured into an independent device for equipping with an existing waste container or built-in a waste container as illustrated in the above described first and second preferred embodiments.

In accordance with another aspect of the present invention, a dual-band ultraviolet sterilization and deodorization arrangement is provided for the waste container including the container body 2 having the container opening 20 and the inner cavity 21 for storing waste and the container lid 1 configured to be mounted on top of the container opening 20 to cover the inner cavity 21 of the container body 2, wherein the dual-band ultraviolet sterilization and deodorization arrangement comprises the isolation chamber 3, the dual-band ultraviolet lamp tube 33 and the control circuit 13.

The isolation chamber 3 comprises the reflector housing 31, configured for installing below the container lid 1 of the waste container and positioned above the container opening 20 of the container body 2, has the light-transmitting window 32 formed in a lower side thereof. The dual-band ultraviolet lamp tube 33 is arranged in the reflector housing 31 and configured to generate the ultraviolet light rays, including the direct sterilization ultraviolet light wave having a wave length between 253.7 nm to 254 nm and the ozone sterilization ultraviolet light wave having a wave length between 165 nm to 200 nm, such that the ultraviolet light rays are arranged to propagate out through the light-transmitting window 32. The control circuit 13 is configured to selectively turn on the dual-band ultraviolet lamp tube 33 to propagate the ultraviolet light rays and turn off the dual-band ultraviolet lamp tube 33 to stop propagating the ultraviolet light rays.

According to the first preferred embodiment as illustrated in FIG. 1 to FIG. 5, the container lid 1 has a side pivotally connected to a top edge of the container body 2 through a hinge mechanism 4 in such a manner that the container lid 1 is able to be flipped up about the hinge mechanism 4 to the open state as shown in FIG. 1 to open the container lid 1 with respect to the container body 2, such that the inner cavity 21 is accessible to outside, or to be flipped down about the hinge mechanism 4 to the close state as shown in FIG. 5 to close the container lid 1 with respect to the container body 2, such that the inner cavity 21 is isolated from outside by the container lid 1. A receiving shell 101 is provide to a bottom side of the container lid 1, a rear portion of the bottom side adjacent to the hinge mechanism 4 according to the first preferred embodiment, and the reflector housing 31 is fixedly mounted in the receiving shell 101 while the light-transmitting window 32 is positioned a above the container opening 20 and facing the inner cavity 21 of the container body 2 when the waste container is in the close state as shown in FIG. 5.

According to the second preferred embodiment as illustrated in FIGS. 2, 4 and 6-16, the ring shape housing 11 of the container lid 1 comprises the ring shape retainer body 112 shaped and sized to mount on the top edge of the container body 2 and defines the lid opening 10 therein. The ring shape housing 11 further comprises the ring shape shell 111 coupled with the ring shape retainer body 112 to define the receiving cavity 110 therein. A rear side of the lid 12 is pivotally connected to a rear side of the ring shape shell 111 by means of a hinge mechanism 4, as shown in FIG. 8 and FIG. 15, such that the lid 12 is able to be flipped up about the hinge mechanism 4 to the open state to open the container lid 1 with respect to the container body 2 such that the inner cavity 21 is accessible to outside, or to be flipped down about the hinge mechanism 4 to the close state to close the container lid 1 with respect to the container body 2 such that the inner cavity 21 is isolated from outside by the lid 12 of the container lid 1. The reflector housing 31 is fixedly mounted in the receiving cavity 110, in a rear portion below the hinge mechanism 4 according to the second preferred embodiment, while the light-transmitting window 32 is positioned above the container opening 20 and facing the inner cavity 21 of the container body 2 no matter the lid 12 is in the open state with respect the ring shape shell 111 and the container body 2 or the close state with respect to the ring shape shell 111 and the container body 2 as shown in FIG. 8.

In particular, the reflector housing 31 has the opening 30 in the lower side and the light-transmitting window 32 is made of transparent quartz glass fittingly and sealingly mounted at the opening 30 of the reflector housing 31 for facing the inner cavity 21 of the container body 2.

According to both the first and second preferred embodiments, referring to FIGS. 3-5, 8, and 15-16, the dual-band ultraviolet lamp tube 33 comprises two lamp tube bodies 331, 332 configured to propagate the direct sterilization ultraviolet light rays (253.7 nm to 254 nm wavelength) and the ozone sterilization ultraviolet light rays (165 nm to 200 nm wavelength) respectively, wherein the light-transmitting window 32 is preferred to have a size larger than the two lamp tube bodies 331, 332 so that the ultraviolet light rays propagating from the lower sides of the two lamp tube bodies 331, 332 are transmitting through the light-transmitting window (transparent quartz glass) 32 into the inner cavity 21 of the container body 2.

Figure 3:
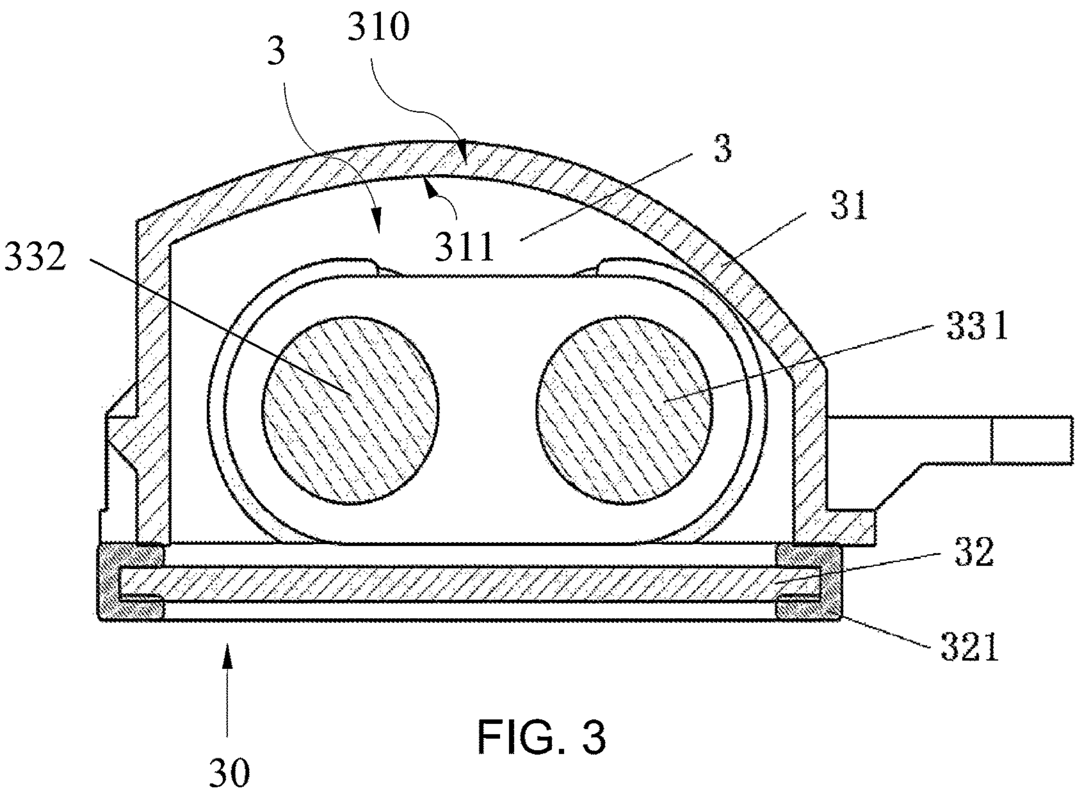
FIG. 3 is a structural sectional view of an isolation chamber of the dual-band sterilization and deodorization arrangement for waste container according to the present invention.
Figure 4:
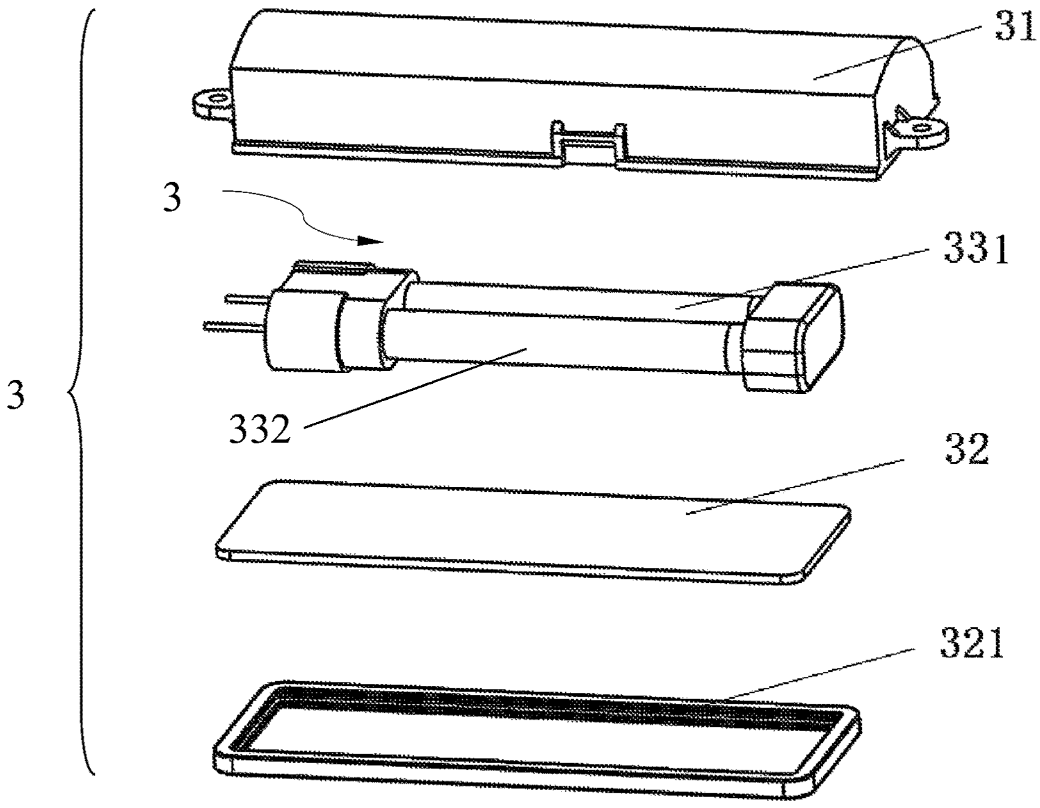
FIG. 4 is an exploded structural perspective view of the isolation chamber of the dual-band sterilization and deodorization arrangement for waste container according to the present invention.

In addition, as shown in FIGS. 3, 5 and 15, an upper side 310 of the reflector housing 31 is a curve surface coated with a reflective surface 311 arranged to face the dual-band ultraviolet lamp tube 33 and the light-transmitting window 32, such that a portion of the ultraviolet light rays propagating upwards is reflected by the reflecting surface 311 to propagate downwards through the light-transmitting window 32 into the inner cavity 21 of the container body 2. Accordingly, by means of the incorporation of the light-transmitting window 32 and the reflective surface 311 of the reflector housing 31, a maximum amount of ultraviolet light rays generated from the dual-band ultraviolet lamp tube 33 is capable of propagating into the inner cavity 21 of the container body 2.

Referring to FIGS. 5, 6, 8 and 10-13, since the waste is disposed into the inner cavity 21 of the container body 2 through the container opening 20, the isolation chamber 3 and the dual-band ultraviolet lamp tube 33 installed therein are preferred to be arranged around the lid opening 10 and positioned above the container opening 20 to ensure the ultraviolet light rays generated from the dual-band ultraviolet lamp tube 33 through the light-transmitting window 32 are propagated into the inner cavity 21 of the container body 2. According to the first preferred embodiment, as shown in FIG. 5, the isolation chamber 3 is preferred to be arranged at a bottom rear portion below the lid 12 of the container lid 1 while the light-transmitting window 32 is positioned above the container opening 20. According to the second preferred embodiment, as shown in FIGS. 8, 12 and 13, the isolation chamber 3 is preferred to be arranged at a bottom rear portion of the ring shape retainer body 112 of the container lid 1 while the light-transmitting window 32 is positioned above the container opening 20 of the container body 2.

According the first preferred embodiment, the control circuit 13 is configured to selectively control the dual-band ultraviolet lamp tube 33 to turn off to stop generating the ultraviolet light rays while the container lid 1 is opened with respect to the container body 2 and to turn on to generate the ultraviolet light rays while the container lid 1 is closed with respect to the container body 2. According the second preferred embodiment, the control circuit 13 is configured to selectively control the dual-band ultraviolet lamp tube 33 to turn off to stop generating the ultraviolet light rays while the lid 12 of the container lid 1 is opened with respect to the ring shape shell 111 and the container body 2 and to turn on to generate the ultraviolet light rays while the lid 12 of the container lid 1 is closed with respect to the ring shape shell 111 and the container body 2.

According to both the first and second preferred embodiments, the control circuit 13 comprises at least one detecting control element 131 (133), and at least one control driving element 132 (134), which are installed on the container body 2 and the container lid 1 respectively in such a manner that when the container lid 1 is opened, the control driving element 132 leaves a detection range of the detecting control element 131, the control circuit 13 controls the dual-band ultraviolet lamp tube 33 to turn off to stop generating the ultraviolet light rays, and that when the container lid 1 is closed in place, the detecting control element 132 detects an approaching of the control driving element 131 and the control circuit 13 controls the dual-band ultraviolet lamp tube 33 to turn on to generate the ultraviolet light rays.

As mentioned above, the at least one detecting control element 131 is embodied as control switch selected from a group consisting of Hall element, position limiting switch and an angle sensor, and the control driving element 132 is embodied as a magnet.

The control driving element 132 is provided under the container lid 1 and the detecting control element 131 is provided in the waste container where the detecting control element 131 is able to detect a distant between the detecting control element 131 and the control driving element 132 to determine whether the contain lid 1 is in the close state or the open state with respect to the container body 2.

Referring to FIG. 5, according to the first preferred embodiment, the control driving element (magnet) 132 is installed at a rear edge of the container lid 1 which is overlapped with a rear top edge of the container body 2, where the detecting control element (Hall element) 131 is installed thereon, when the container lid 1 is in the close state as shown in FIG. 5. Accordingly, when the container lid 1 is flipping up to open the container body 2, the control driving element 132 is moving away from the detecting control element 131, and a signal is sent from the detecting control element 131 to trigger the ultraviolet lamp tube driver circuit 34, which is powered by an external power source or internal power source such as one or more batteries (not shown in Figures), to turn off the dual-band ultraviolet lamp tube 33 to cease the generation of the ultraviolet light rays to prevent causing harm to human skin eyes while the inner cavity is accessible to outside. The dual-band ultraviolet lamp tube 33 is always remained in a turn-off state.

Also, when the container lid 1 is flipping down until the container lid 1 is closed in place with respect to the container body 2 as shown in FIG. 5, the control driving element 132 is moving towards the detecting control element 131 until it is overlapped on the detecting control element 131, i.e. the container lid 1 is fully closed in place to isolate the inner cavity 21 of the container body 2 from outside, the detecting control element 131 detects the approaching of the control driving element 132 and sends out another signal to trigger the ultraviolet lamp tube driver circuit 34 to turn on the dual-band ultraviolet lamp tube 33 to generate ultraviolet light rays to propagate into the inner cavity 21 of the container body 2.

It is worth mentioning that the installation locations of the pair of detecting control element 131 and the control driving element 132 can be exchanged.

Referring to FIG. 8, according to the second preferred embodiment, the lid 12 of the container lid 1 is configured to open or close the lid opening 10 and the container opening 20 simultaneously. The control circuit 13 comprises two pairs of detecting control element 131, 133 and control driving element 132, 134, wherein the two detecting control elements 131, 133 are installed on the ring shape shell 11 and the two control driving elements 132, 134 are installed on the container body 2 and the lid 12 respectively, such that when one of the detecting control elements 131, 133 leaves the corresponding control driving element 132, 134 while either the lid 12 or the ring shape shell 11 is opened with respect to the container body 2, the control circuit 13 controls the dual-band ultraviolet lamp tube 33 to turn off to stop generating the ultraviolet light rays, and that when both the ring shape shell 11 and the lid 12 are closed in place with respect to the container body 2, the detecting control elements 131, 133 detect an approaching of the corresponding control driving element 132, 134 and the control circuit 13 controls the dual-band ultraviolet lamp tube 33 to turn on to generate the ultraviolet light rays.

In particular, referring to FIG. 8, the first pair of the detecting control element 131 and the control driving element 132 are installed to a front edge of the ring shape shell 11 and a front edge of the lid 12 respectively so as to control the turn-on and turn-off operation of the dual-band ultraviolet lamp tube 33 with respect to the closing and opening of the lid 12 with respect to the container body 2. The second pair of the detecting control element 133 and the control driving element 134 are installed to a rear portion of the ring shape shell 11 (a rear edge of the ring shape retainer body 112 of the ring shape shell 11) and a rear top edge of the container body 2 respectively.

Accordingly, referring to FIG. 8, when the container lid 1 is separated from the container body 2, such as detaching the ring shape shell 11 upwards from the container body 2, the control driving element 134 leaves a detection range of the detecting control element 133 and the detecting control element 133 sends a signal to trigger the ultraviolet lamp tube driver circuit 34 of the control circuit 13 to turn off the dual-band ultraviolet lamp tube 33 to stop generating the ultraviolet light rays to prevent causing harm to human skin and eyes. Also, when the lid 12 is operated to flip up to open the container body 2, i.e. the inner cavity 21 of the container body 2 is accessible to outside through the lid opening 10 and the container opening 20, the control driving element (e.g. magnet) 132 leaves the detection range of the detecting control element 131 (e.g. Hall element) and the detecting control element 131 generates a sign to trigger the ultraviolet lamp tube driver circuit 34 of the control circuit 13 to turn off the dual-band ultraviolet lamp tube 33 to stop generating the ultraviolet light rays to prevent causing harm to human skin and eyes.

When container lid 1 is placed on the container body 2, i.e. the ring shape shell 11 is normally mounted on the container body 2, and the lid 12 is flipping down until the lid 12 is closed in place with respect to the ring shape shell 11 and the container body 2 as shown in FIG. 8, the control driving element 132 is moving towards the detecting control element 131 until it is overlapped on the detecting control element 132, i.e. the lid 12 is fully closed in place to isolate the inner cavity 21 of the container body 2 from outside, the detecting control element 131 detects the approaching of the control driving element 132 and sends out a signal to trigger the ultraviolet lamp tube driver circuit 34 to turn on the dual-band ultraviolet lamp tube 33 to generate ultraviolet light rays to propagate into the inner cavity 21 of the container body 2. In other words, only while these two conditions are met at the same time, that is both the lid 12 and the ring shape shell 11 are closed in place, the control circuit 13 controls the dual-band ultraviolet lamp tube 33 to turn on and operate, or otherwise, the dual-band ultraviolet lamp tube 33 is preferred to be remained in the turn-off state.

In accordance with another aspect of the invention, a sterilization and deodorization method for the waste container is provided, the method comprising:

(a) turning on the dual-band ultraviolet lamp tube 33, sealed in the isolation chamber 3 provided below the container lid 1 of the waste container 2, to generate ultraviolet light rays, including the direct sterilization ultraviolet light wave having a wavelength between 240 nm to 280 nm, preferably 253.7 nm to 254 nm, and the ozone sterilization ultraviolet light wave having a wavelength between 165 nm to 200 nm, preferably 185 nm, propagating through the light-transmitting window 32 of the isolation chamber 3 into the inner cavity 31 of the waste container, while the container lid 1 is in a close state with respect to the container body 2; and (b) turning off the dual-band ultraviolet lamp tube 33 to stop generating the ultraviolet light rays while the inner cavity 21 of the container body 2 is accessible to outside.

In which, in the step (b), the inner cavity 21 of the container body is accessible to outside when the container lid 1 is opened with respect to the container body 2 and/or the ring shape shell is separated from the container body.

Figure 16:
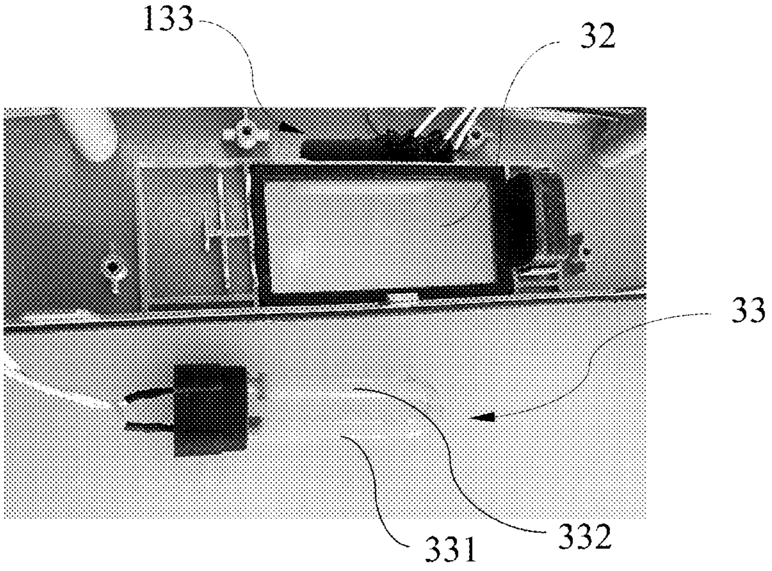
FIG. 16 is an exploded view of the ultraviolet lamp tube and the ultraviolet lamp mount of the ultraviolet sterilization and deodorization arrangement of the sterilization and deodorization waste container according to the second preferred embodiment of the invention.

According to the above first and second preferred embodiments, the dual-band ultraviolet lamp tube 33 can be a cold cathode dual-band ultraviolet lamp tube which comprises a U-shape sealed glass tube, as shown in FIG. 16, forming the two lamp tube bodies 331, 332 configured to propagate the direct sterilization ultraviolet light rays (253.7 nm to 254 nm wavelength) and the ozone sterilization ultraviolet light rays (165 nm to 200 nm wavelength) respectively, wherein the glass tube is preferred to be quartz tube. A gas mixture (usually a noble gas like argon or neon is contained in the sealed glass tube at low pressure. Inside the sealed glass tube, there are two separate cathodes (emission electrodes) made of different materials and are surrounded by a phosphor coating (for example) to produce the direct sterilization ultraviolet light rays (253.7 nm to 254 nm wavelength) and the ozone sterilization ultraviolet light rays (165 nm to 200 nm wavelength), respectively, when excited by the electrons emitted from the cathodes. Also, there are anodes positioned at each end of the tube to complete the electrical circuit and electrical connections provided for powering the dual-band ultraviolet lamp tube 33.

Figure 17:
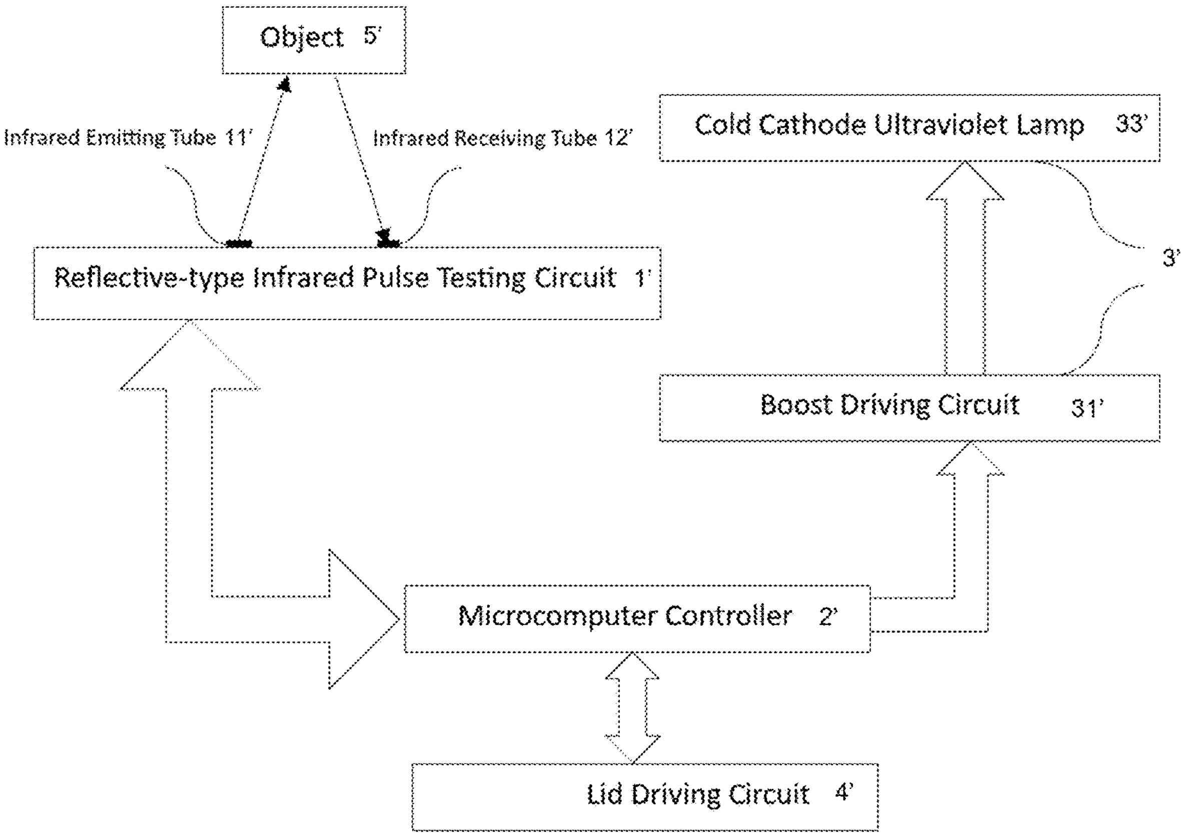
FIG. 17 is a schematic diagram of a control method of induction waste container with cold cathode ultraviolet lamp sterilization and deodorization according to the above preferred embodiment of the present invention.
Figure 18:
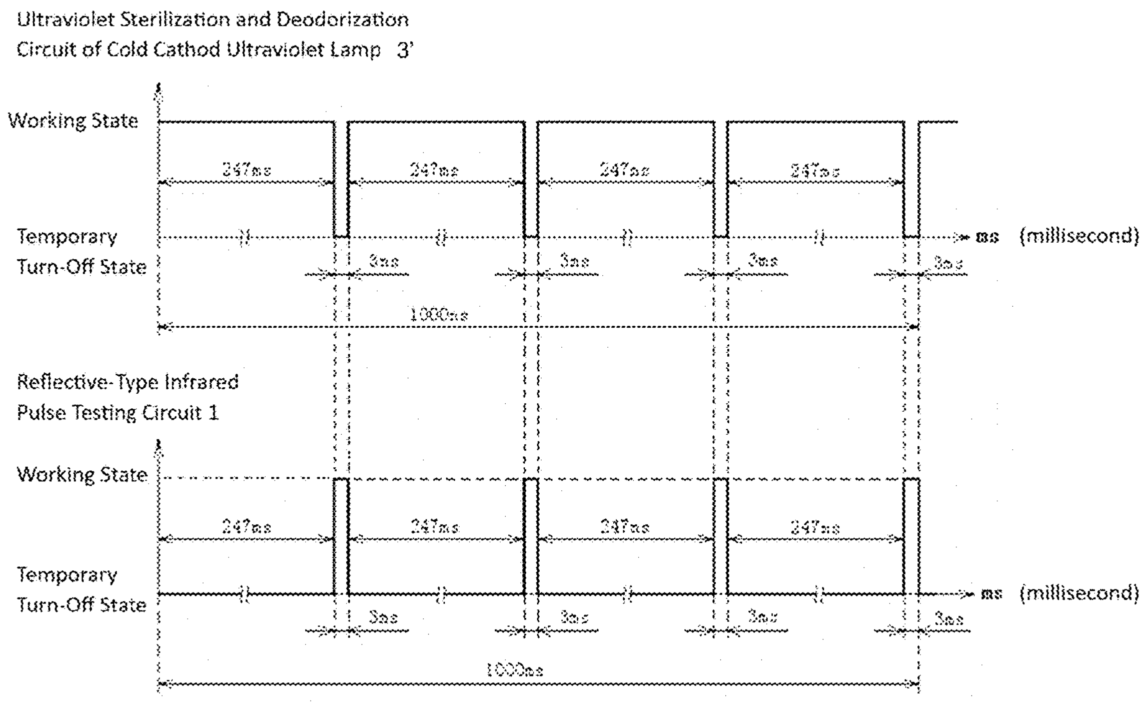
FIG. 18 is a schematic diagram illustrating a working sequence of an infrared pulse testing circuit when an ultraviolet sterilization and deodorization circuit enters a working state of a working cycle of the circuit control method of induction waste container of sterilizing and deodorizing with cold cathode ultraviolet lamp sterilization and deodorization according to the above preferred embodiment of the present invention.
Figure 19:
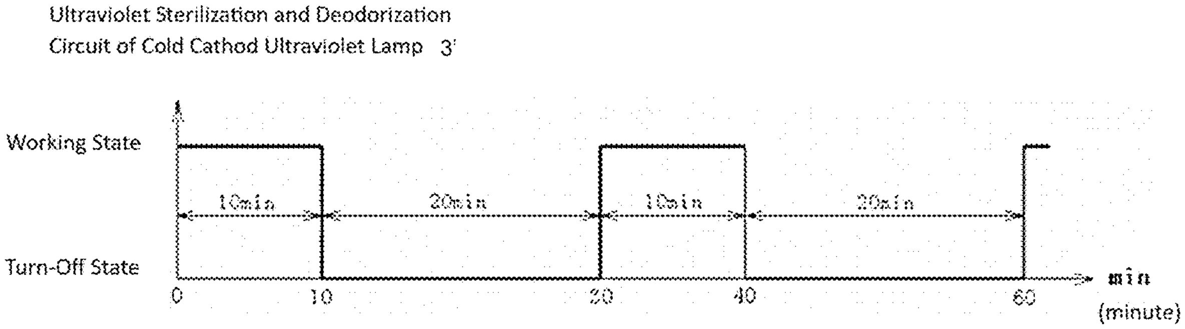
FIG. 19 is a schematic diagram illustrating an intermittent working sequence of the ultraviolet sterilization and deodorization circuit during a standby state of closing the lid of the circuit control method of induction waste container of sterilizing and deodorizing with cold cathode ultraviolet lamp sterilization and deodorization according to the above preferred embodiment of the present invention.

Referring to FIG. 17 to FIG. 19, the dual-band ultraviolet lamp tube 33 is embodied as a cold cathode ultraviolet lamp 33' and a control method of the induction waste container (as shown in FIG. 6 to FIG. 16), is illustrated, wherein a control circuit comprises an infrared pulse testing circuit 1', an microcomputer controller 2', an ultraviolet sterilization and deodorization circuit 3' of the cold cathode ultraviolet lamp 33', and a lid driving circuit 4', wherein the sterilization and deodorization circuit of cold cathode ultraviolet lamp 3' and the lid driving circuit 4' are connected with the microcomputer controller 2' 2'.

The infrared pulse testing circuit 1' is a reflective-type infrared pulse testing circuit, which comprises an infrared emitting tube 11' and an infrared receiving tube 12'. The microcomputer controller 2' controls a coordinated work of each circuit of the present invention. The ultraviolet sterilization and deodorization circuit 3' includes a boost driving circuit 31' and a dual-band cold cathode ultraviolet lamp 33', wherein the boost driving circuit 31' converts a safety low-voltage power supply into a power supply of about 370V for the dural-band cold cathode ultraviolet lamp 33' for use, and the lid driving circuit 4' is configured to drive the opening and closing of the container lid. In order to prevent ultraviolet rays from injuring human eyes and skin, only when the waste container is in a lid closing standby state, the ultraviolet sterilization and deodorization circuit 3' is allowed to work. When the ultraviolet sterilization and deodorization circuit 3' works, the induction waste container should have the function of induction opening of the lid. Because the ultraviolet sterilization and deodorization circuit 3' has a relatively long continuous working time and the lid is not suitable to be induced to open. It may cause inconvenience to the use of induction waste container.

During the standby state of closing the container lid 1 and the ultraviolet sterilization and deodorization circuit 3' is in the working state: When the reflective-type infrared pulse testing circuit 1' is required to work, the microcomputer controller 2' controls the ultraviolet sterilization and deodorization circuit 3' in a temporary closing state, and thus after the reflective-type infrared pulse testing circuit 1' completes the test, the reflective-type infrared pulse testing circuit 1' is turned off and the ultraviolet sterilization and deodorization circuit 3' is turned on immediately if there is no object 5' approaching an induction window of the induction waste container, such that the interference of the ultraviolet sterilization and deodorization circuit 3' to the reflective-type infrared pulse testing circuit 1' is avoided, and that, at the same time, a working time of the reflective-type infrared pulse testing circuit 1' is much less than the working time of the sterilization and deodorization circuit of cold cathode ultraviolet lamp 3'.

Because the sterilization and deodorization circuit of cold cathode ultraviolet lamp 3' is preferred to last for more than 10 minutes for an ideal sterilization effect. Also, the ultraviolet irradiation requires a predetermined amount of time to kill the bacteria and the concentration of ozone requires a predetermined amount of time to accumulate.

Accordingly, the relatively short temporary turn-off of the sterilization and deodorization circuit of cold cathode ultraviolet lamp 3' during its working state is almost equivalent to the sterilization and deodorization circuit of cold cathode ultraviolet lamp 3' is working continuously, that basically does not affect the continuity of ultraviolet radiation and the change of ozone concentration.

Referring to FIG. 18 of the drawings, when the container lid 1 or lid 12 of the induction waste container is closed and the sterilization and deodorization circuit 3' is in the working state, in each one-second cycle of the present embodiment, the reflective-type infrared pulse testing circuit 1' works 4 times, wherein the working time of each time is 3 ms and an infrared detection pulse is emitted by the infrared emitting tube 11' to an induction area.

To each emission of the infrared detection pulse, the time of the temporary turn-off of the sterilization and deodorization circuit of cold cathode ultraviolet lamp 3' is 3 ms, while an interval time is 247 ms. In each one-second cycle, the reflective-type infrared pulse testing circuit 1' emits an average of 4 infrared detection pulses, which can ensure the induction waste container cannot respond slowly and not to take too long. That is 4 infrared detection pulses is emitted per second while the sterilization and deodorization circuit of cold cathode ultraviolet lamp 3' is temporarily closed for 3 ms each time, such that a working time ratio of the sterilization and deodorization circuit of cold cathode ultraviolet lamp 3' is 98.8% through computation. Such high working time ratio is equivalent to that the sterilization and deodorization circuit of cold cathode ultraviolet lamp is almost continuously working and basically does not affect the continuity of ultraviolet radiation and the change of ozone concentration.

In the preferred embodiment, a U-shaped 3.3-watt dual-band cold cathode ultraviolet lamp 33' is embodied and its life span is about 13000 hours, wherein the working cycle of the dual-band cold cathode ultraviolet lamp 33' is 10 minutes, the turn-off cycle is 20 minutes. As shown in FIG. 19, it works repeatedly in an intermittence manner, such that calculated as 24 hours a day and the dual-band cold cathode ultraviolet lamp 33' actually works for up to 8 hours a day, the dual-band cold cathode ultraviolet lamp 33' can be used for more than 4 years, that basically meets the market requirement. Also, at the same time, that will not cause the ozone concentration in the waste container to be too high, wherein a small portion of the ozone will diffuse out when the lid is opened (a specific gravity of ozone is heavier than the air), so that the diffused ozone concentration will not exceed the safety and health standard of 1 ppm. While comprehensively considering that the time of most bacterial reproduction generation is 20~30 minutes, as well as considering that ozone is an unstable gas and its semi-decay phase is only about 30 minutes, the dural-band cold cathode ultraviolet lamp 33' is preferred to continue to work for 10 minutes and stop working for 20 minutes according to the preferred embodiments.

During a standby state of closing the lid 1 or lid 12 of the induction waste container, the sterilization and deodorization circuit of cold cathode ultraviolet lamp 3' may be in working state or turn-off state. When the object 5' is approaching an induction window of the induction waste container, the infrared detection pulse emitted by infrared emitting tube 11' is reflected by a surface of the object 5' and received by infrared receiving tube 12', wherein the weak received signal is then amplified by an amplification of reflective-type infrared pulse testing circuit 1' and fed back to microcomputer controller 2'. Then, the microcomputer controller 2' controls the boost driving circuit 31' to stop working, thereby cutting off a high-voltage power supply of the dual-band cold cathode ultraviolet lamp 32', making the sterilization and deodorization circuit of cold cathode ultraviolet lamp 3' in the turn-off state, avoiding ultraviolet radiation hurting human eyes and skin, and then controlling the container lid to open.

After the waste is disposed in the induction waste container, the container lid 1 is closed and the sterilization and deodorization circuit of cold cathode ultraviolet lamp 3' returns to the original working state or closing state, wherein the working state time or the closing state time of the sterilization and deodorization circuit of cold cathode ultraviolet lamp 3' is computed as an accumulation time that lasts the previous cycle. Because only a few seconds is taken for the induction waste container to open the lid 12, from the induction trigger to open and to the closing of the lid 12 after the waste is disposed in the induction waste container, the sterilization and deodorization circuit of cold cathode ultraviolet lamp 3' returns to its original state and continues the accumulation time with the previous cycle, that basically does not affect the overall sterilization and deodorization effect.

Accordingly, the control method includes steps of:

S1: setting a working cycle and a turn-off cycle of the ultraviolet sterilization and deodorization circuit 3', wherein the working cycle is greater than 9 minutes, and setting the infrared pulse testing circuit 1' to work n times per second in the working cycle of the ultraviolet sterilization and deodorization circuit 3', wherein each the working time of the infrared pulse testing circuit 1' is 1 ms~8 ms, wherein a time between two adjacent operations of the infrared pulse testing circuit 1' is a time interval;

S2: when the lid 12 is closed and standby, entering a working state by the ultraviolet sterilization and deodorization circuit 3', and starting to time the working cycle;

S3: after the time interval, sending a trigger signal from the microcomputer controller 2' to make the ultraviolet sterilization and deodorization circuit 3' in a temporary turn-off state, and, during the temporary turn-off state, triggering the infrared pulse testing circuit by the microcomputer controller 2' to start working and emitting infrared detection pulses by the infrared pulse testing circuit 1';

S4: when the infrared pulse testing circuit 1' is working, if there is no object 5' approaching the induction waste container, turning off the infrared pulse testing circuit 1' after the working time of the infrared pulse testing circuit 1' is ended, and then controlling the ultraviolet sterilization and deodorization circuit to start by the microcomputer controller 2', wherein the step S3 is returned until the working cycle of the ultraviolet sterilization and deodorization circuit 3' is ended; and S5: turning off the ultraviolet sterilization and deodorization circuit 3', starting to time the turn-off cycle, and returning to the step S2 after the turn-off cycle ends.

Accordingly, the infrared pulse testing circuit emits the infrared detection pulses during its working time, and the ultraviolet sterilization and deodorization circuit 3' is temporarily closed for 1 ms~8 ms time. Taking an one-second cycle as an example, the infrared pulse testing circuit 1' emits infrared detection pulses 3 times in each one-second cycle, and the ultraviolet sterilization and deodorization circuit 3' is temporarily closed for a time of 1 ms each time, in which a working time ratio of the ultraviolet sterilization and deodorization circuit 3' is 99.7% through computation; if the infrared pulse testing circuit 1' emits infrared detection pulses 8 times in each one-second cycle and the ultraviolet sterilization and deodorization circuit 3' is temporarily turned off for 8 ms, the working time ratio of the ultraviolet sterilization and deodorization circuit 3' is 93.6% through computation. Such high working time ratio is equivalent to that the sterilization and deodorization circuit 3' is almost in a continuous working state, which basically does not affect a continuity of ultraviolet irradiation and a change of ozone concentration.

The working time of the present invention based on the infrared pulse testing circuit 1' is much smaller than the working time of the sterilization and deodorization circuit 3', while the ultraviolet sterilization and deodorization circuit 3' adopts a predetermined number of temporary turn-off for extremely short time, such that the two working times thereof are being embedded control, that is embedding the working time of the infrared pulse testing circuit 1' in the working cycle of the ultraviolet sterilization and deodorization circuit 3', so as to effectively implement the separation and integration of time during the working state of the ultraviolet sterilization and deodorization circuit 3' and the infrared pulse testing circuit 1'. Therefore, on one hand, the ultraviolet sterilization and deodorization circuit 3' will not interfere with the infrared pulse testing circuit 1' to ensure the working stability of infrared pulse testing circuit and the reliability of the induction opening of the lid; on the other hand, the ultraviolet sterilization and deodorization circuit 3' is basically maintained in a continuous working state during working hours that ensures the continuity of ultraviolet irradiation, so that the ultraviolet sterilization time and the accumulation requirements of ozone concentration can be satisfied. In addition, the ultraviolet sterilization and deodorization circuit 3' is set with a turn-off cycle, which can effectively extend the service life of the ultraviolet lamp and can effectively control the ozone concentration in the waste container.

The present invention may be further specified as:

The number of infrared detection pulses emitted by the infrared pulse testing circuit 1' in the working cycle of the ultraviolet sterilization and deodorization circuit 3' is 3~8 times per second, and the working time ratio of the ultraviolet sterilization and deodorization circuit 3' is greater than 93.6%.

Regarding the ensuring of the infrared induction opening of the lid 12, the working time of the ultraviolet sterilization and deodorization circuit is ensured to have a high working time ratio, so as to ensure the continuity of ultraviolet irradiation and the accumulation of ozone concentration.

During the ultraviolet sterilization and deodorization circuit 3' is in its working cycle, when the infrared pulse testing circuit 1' works, such as an approaching object 5' is detected through the emitted infrared detection pulse(s), the infrared detection pulse(s) is reflected by a surface of the object 5', and then the infrared pulse testing circuit 1' processes the reflected signal from the object 5' and feeding back to a microcomputer controller 2'. The microcomputer controller 2' controls the ultraviolet sterilization and deodorization circuit 3' being maintained in the turn-off state, such that the working cycle temporarily stops timing, the microcomputer controller 2' further triggers the lid driving circuit 4', and the lid 12' is opened under the control of the lid driving circuit 4'. After the lid 12' is closed, the working cycle continues to time.

Because it only takes a few seconds from the induction trigger to open the lid 12 of the induction waste container and to close the lid 12 after disposal of the waste in the induction waste container, the ultraviolet sterilization and deodorization circuit 3' returns to its original working state after closing the lid 12 and continues the accumulation of the working cycle, that can not only ensure the integrity of the working cycle, but also basically will not affect the overall sterilization and deodorization effect while ensuring the induction opening of the lid 12 being convenient to use.

During the ultraviolet sterilization and deodorization circuit 3' is in a turn-off state of the turn-off cycle, if an approaching object 5' is detected through the emitted infrared detection pulse(s), the infrared detection pulse(s) is reflected by a surface of the object 5', and then the infrared pulse testing circuit 1' processes the reflected signal from the object and feeding back to a microcomputer controller 2'. Then, the turn-off cycle temporarily stops timing and the microcomputer controller 2' further triggers the lid driving circuit 1' to open the lid 12 under a control by the lid driving circuit 1'. After the lid 12 is closed, the turn-off cycle in the microcomputer controller 2' continues timing.

Likewise, the short opening and closing of the lid 12 will not affect the integrity of the turn-off cycle. On the other hand, because ozone is an unstable gas, having a semi-decay phase, a fixed length of the turn-off cycle can be timely started after ozone is consumed to a certain extent to ensure the sterilization and deodorization effect.

The working cycle is 10~30 minutes, and the turn-off cycle is 20~60 minutes.

In order to ensure the sterilization and deodorization effect, the present invention further takes a predetermined amount of time for ultraviolet irradiation to kill bacteria, and the concentration of ozone also needs a predetermined amount of time to accumulate, so that the ultraviolet sterilization and deodorization circuit 2' is preferred to continue to work for more than 10 minutes. Considering the rate of bacterial growth and ozone consumption, the turn-off cycle should be less than 60 minutes.

In view of above, the present invention provides a control method of induction waste container with cold cathode ultraviolet lamp sterilization and deodorization, which embeds the working time of the infrared pulse testing circuit 1' into the working time of the ultraviolet sterilization and deodorization circuit 3', so as to effectively implement the separation and integration of time during the working state of the ultraviolet sterilization and deodorization circuit 3' and the infrared pulse testing circuit 1', avoid the interference of the ultraviolet sterilization and deodorization circuit 3' with respect to the infrared test circuit 1', accomplish that the lid 12 can be opened inductively at any time in the standby state, prolong the service life of the cold cathode ultraviolet lamp 33', control the ozone concentration in the waste container, and achieve a more ideal sterilization and deodorization effect simultaneously. The present invention has good safety performance, simple and reliable circuit structure, low cost, and strong practical application value.

Figure 20:
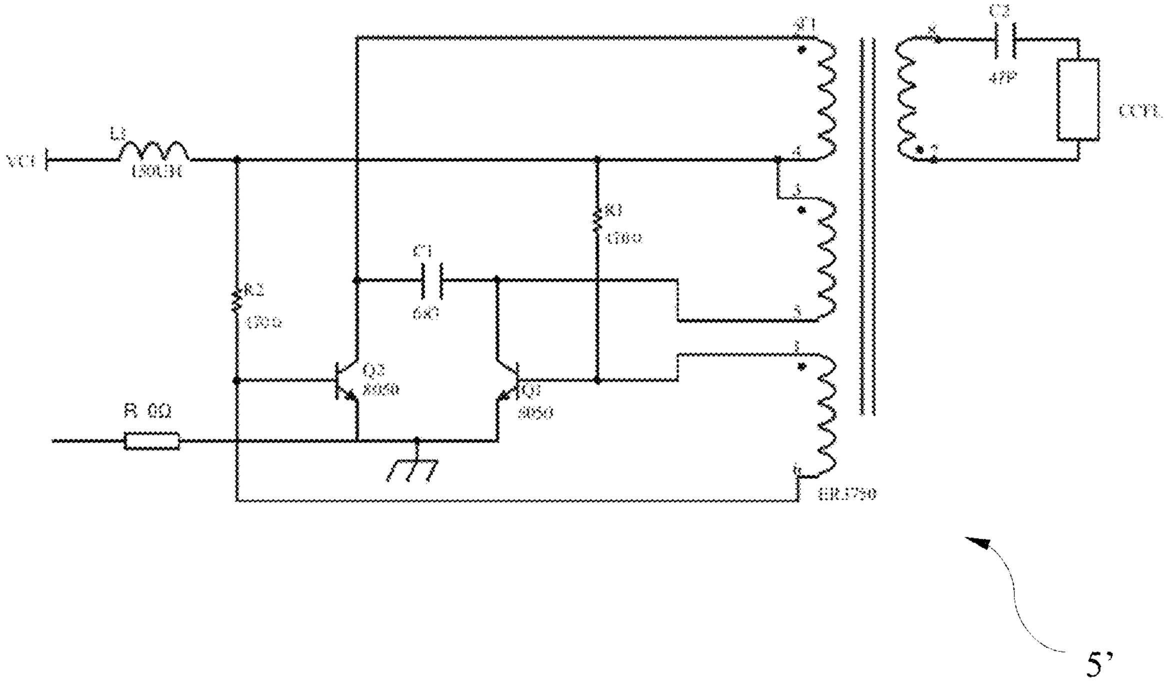
FIG. 20 is circuit diagram of the AC power source of the sterilization and deodorization waste container according to the preferred embodiments of the present invention.

As shown in FIG. 20, an AC power source 5' is arranged to supply electrical power to the dual-band ultraviolet lamp tube 33, the control circuit 13, the ultraviolet lamp tube driving circuit 34, and the control switch 131 of the sterilization and deodorization waste container according to the second preferred embodiment. Referring to FIG. 16, when the alternating current (AC) power source 5' is connected to the two terminals of the U shape dual-band ultraviolet lamp tube 33, the polarity of the voltage across the cathode and anode terminals alternates periodically. During one half of the AC cycle, the cathode becomes negative relative to the anode, causing electrons to be emitted from the cathode towards the anode. During the other half of the cycle, the polarity reverses, and the anode becomes negative relative to the cathode, causing the electrons to be attracted back towards the anode again. This alternating flow of electrons back and forth between the cathode and anode occurs rapidly, typically at the frequency of the AC power source (e.g., 50 Hz or 60 Hz). As a result, UV radiation is emitted continuously during each half-cycle of the AC power, making the tube operate efficiently.

According to the present invention, the dural-band ultraviolet lamp tube 33 is configured to produce the ultraviolet light rays with the preferable wavelength of 254 nm and 185 nm, wherein the ultraviolet light wave with preferable 254 nm wavelength (also known as short-wave sterilized ultraviolet light) has a high photon energy and irradiates into the waste disposed in the inner cavity 21 of the container body 2, that can penetrate the cell membrane and nucleus of microorganisms, break the molecular bonds of their DNA, and make them lose their ability to replicate or become inactive and die, wherein the ultraviolet light wave with preferable 185 nm wavelength irradiates the air, turning the oxygen into the air into ozone, which has a strong oxidation effect and can effectively kill bacteria. It is appreciated that the diffusivity of ozone can make the odor fill the entire inner cavity 21 of the container body 2 that can just make up for the blind angles of the ultraviolet light rays that only propagate along a straight line.

The above description is merely preferred embodiments of the invention and is not intent to limit the invention, and any modification, equivalent substitution, improvement, and etc. made within the spirit and principles of the invention should be included within the scope of the claimed invention.

One skilled in the art will understand that the embodiment of the present invention as shown in the drawings and described above is exemplary only and not intended to be limiting.

What is claimed is:

1. A waste container, comprising:

a container body having an inner cavity;

a lid arranged on top of the inner cavity of the container body;

an isolation chamber arranged below the lid and positioned above the inner cavity of the container body, wherein the isolation chamber comprises a reflector housing and a light-transmitting window facing the inner cavity of the container body;

a dual-band ultraviolet lamp tube, which is mounted in the isolation chamber, configured to generate ultraviolet light rays for direct sterilization and ultraviolet light rays for ozone sterilization and deodorization to propagate into the inner cavity of the container body through the light-transmitting window of the isolation chamber; and a control circuit configured to selectively control the dual-band ultraviolet lamp tube to propagate the ultraviolet light rays into the inner cavity of the container body and stop propagating the ultraviolet light rays into the inner cavity of the container body, the control circuit comprising:

an infrared pulse testing circuit configured to detect an object approaching the waste container when the infrared pulse testing circuit is turned on;

a microcomputer controller;

an ultraviolet sterilization and deodorization circuit configured to activate the dual-band ultraviolet lamp tube when the ultraviolet sterilization and deodorization circuit is turned on; and a lid driving circuit configured to open the lid in response to detection by the infrared pulse testing circuit, wherein the microcomputer controller is configured to operate the control circuit, when the lid is closed, such that:

the ultraviolet sterilization and deodorization circuit is turned on for a duration of a working time of the sterilization and deodorization circuit, the ultraviolet sterilization and deodorization circuit is temporarily turned off when the working time of the sterilization and deodorization circuit ends, the infrared pulse testing circuit is turned on for a working time of the infrared pulse testing circuit when the working time of the sterilization and deodorization circuit ends, the infrared pulse testing circuit is then turned off when the working time of the infrared pulse testing circuit ends, and the ultraviolet sterilization and deodorization circuit is immediately turned back on when the working time of the infrared pulse testing circuit ends and no object approaching the sterilization and deodorization waste container was detected by the infrared pulse testing circuit, and wherein the working time of the infrared pulse testing circuit is less than the working time of the sterilization and deodorization circuit.

2. The waste container, as recited in claim 1, wherein the control circuit comprises at least one detecting control element installed on the container body and at least one control driving element arranged below the lid in such a manner that, when the lid is opened to an open state, the control driving element leaves a detection range of the detecting control element, the control circuit controls the dual-band ultraviolet lamp tube to turn off to stop generating the ultraviolet light rays, and when the lid is closed in place to a close state, the detecting control element detects the control driving element and the control circuit controls the dual-band ultraviolet lamp tube to turn on to generate the ultraviolet light rays.

3. The waste container, as recited in claim 2, wherein the control driving element is provided under the lid and the detecting control element is provided in the sterilization and deodorization waste container where the detecting control element is able to detect a distance between the detecting control element and the control driving element to determine whether the lid is in the close state or the open state with respect to the container body.

4. The waste container, as recited in claim 1, wherein the light-transmitting window is positioned above a container opening of the inner cavity of the container body.

5. The waste container, as recited in claim 4, wherein the reflector housing has an opening facing the inner cavity of the container body and the light-transmitting window is made of transparent quartz glass matching the opening of the reflector housing in shape and size and sealingly covering the opening of the reflector housing.

6. The waste container, as recited in claim 1, wherein the ultraviolet light rays for direct sterilization have a wavelength between 253.7 nm and 254 nm and the ultraviolet light rays for ozone sterilization and deodorization have a wavelength between 165 nm and 200 nm.

7. A control method of a sterilization and deodorization waste container, comprising steps of:

(a) generating a direct sterilization ultraviolet light wave, having a wavelength between 240 nm to 280 nm, and an ozone sterilization ultraviolet light wave, having a wavelength between 165 nm to 200 nm by a dual-band ultraviolet lamp tube sealed in an isolation chamber provided below a lid of the sterilization and deodorization waste container;

(b) propagating the direct sterilization ultraviolet light wave and the ozone sterilization ultraviolet light wave into an inner cavity of the sterilization and deodorization waste container, while the lid of the sterilization and deodorization waste container is in a close state with respect to a container body of the sterilization and deodorization waste container;

(c) stopping to propagate the direct sterilization ultraviolet light wave and the ozone sterilization ultraviolet light wave into an inner cavity of the sterilization and deodorization waste container, while the container lid is in an open state with respect to the container body of the sterilization and deodorization waste container;

(d) setting a working cycle and a turn-off cycle of an ultraviolet sterilization and deodorization circuit, wherein the working cycle is greater than 9 minutes, and setting an infrared pulse testing circuit to work n times per second in the working cycle of the ultraviolet sterilization and deodorization circuit, wherein each working time of the infrared pulse testing circuit is 1 ms to 8 ms, wherein a time between two adjacent operations of the infrared pulse testing circuit is a time interval;

(e) when the lid of the sterilization and deodorization waste container is in the close state and during a standby state, entering a working state by the ultraviolet sterilization and deodorization circuit, and starting to time the working cycle;

(f) after the time interval, sending a trigger signal from a microcomputer controller to make the ultraviolet sterilization and deodorization circuit in a temporary turn-off state, and, during the temporary turn-off state, triggering the infrared pulse testing circuit by the microcomputer controller to start working and emitting infrared detection pulses by the infrared pulse testing circuit;

(g) when the infrared pulse testing circuit is working, if no object approaching the sterilization and deodorization waste container is detected, turning off the infrared pulse testing circuit after the working time of the infrared pulse testing circuit is ended, and then controlling the ultraviolet sterilization and deodorization circuit to start by the microcomputer controller, wherein the step (f) is returned until the working cycle of the ultraviolet sterilization and deodorization circuit ends; and (h) turning off the ultraviolet sterilization and deodorization circuit, starting to time the turn-off cycle, and returning to the step (e) after the turn-off cycle ends.

8. The control method, as recited in claim 7, wherein during the standby state in which the lid of the sterilization and deodorization waste container is closed and the ultraviolet sterilization and deodorization circuit is in the working state, when the infrared pulse testing circuit is required to work, the microcomputer controller controls the ultraviolet sterilization and deodorization circuit to enter the temporary turn-off state, and after the infrared pulse testing circuit completes a test, the infrared pulse testing circuit is turned off and the ultraviolet sterilization and deodorization circuit is turned on immediately if no object approaching the sterilization and deodorization waste container is detected, such that an interference of the ultraviolet sterilization and deodorization circuit with the infrared pulse testing circuit is avoided, and the working time of the infrared pulse testing circuit is less than a working time of the sterilization and deodorization circuit.

9. The control method, as recited in claim 8, wherein, while the ultraviolet sterilization and deodorization circuit is in a turn-off state of the turn-off cycle, if an object approaching the sterilization and deodorization waste container is detected through an emitted infrared detection pulse of the infrared pulse testing circuit reflected by a surface of the object and fees back the reflected sign to the microcomputer controller, the infrared pulse testing circuit processes a reflected signal from the object and feeds back the reflected signal to the microcomputer controller, the turn-off cycle temporarily stops timing, and the microcomputer controller further triggers a lid driving circuit to open the lid of the sterilization and deodorization waster container, wherein, after the lid of the sterilization and deodorization waste container is closed, the turn-off cycle in the microcomputer controller continues timing.

10. The control method, as recited in claim 7, wherein the working cycle is greater than or equal to 10 minutes and less than or equal to 30 minutes, and the turn-off cycle is greater than or equal to 20 minutes and less than or equal to 60 minutes.

11. The control method, as recited in claim 9, wherein the infrared pulse testing circuit emits the infrared detection pulses during the working time thereof, and the ultraviolet sterilization and deodorization circuit is temporarily turned off for 1 ms to 8 ms.

12. The control method, as recited in claim 7, wherein, when only a few seconds are taken from an induction trigger to open the lid of the sterilization and deodorization waste container and to close the lid of the sterilization and deodorization waste container after disposal of a waste in the sterilization and deodorization waste container, the ultraviolet sterilization and deodorization circuit returns to an original working state thereof after the lid of the sterilization and deodorization is closed and continues accumulation of the working cycle.

* * * * *